US008425536B2

(12) United States Patent
Foerster et al.

(10) Patent No.: US 8,425,536 B2
(45) Date of Patent: Apr. 23, 2013

(54) IMPLANT AND DELIVERY SYSTEM FOR SOFT TISSUE REPAIR

(75) Inventors: Seth A. Foerster, San Clemente, CA (US); George W. White, Corona, CA (US); David Gregoire, Mission Viejo, CA (US)

(73) Assignee: ArthroCare Corporation, Austin, TX (US)

(*) Notice: Subject to any disclaimer, the term of this patent is extended or adjusted under 35 U.S.C. 154(b) by 0 days.

(21) Appl. No.: 13/106,096

(22) Filed: May 12, 2011

(65) Prior Publication Data

US 2011/0213417 A1 Sep. 1, 2011

Related U.S. Application Data

(62) Division of application No. 11/854,235, filed on Sep. 12, 2007, now Pat. No. 7,963,972.

(51) Int. Cl.
*A61B 17/10* (2006.01)

(52) U.S. Cl.
USPC .......... 606/139; 606/232

(58) Field of Classification Search .......... 606/139–145, 606/213, 215, 232
See application file for complete search history.

(56) References Cited

U.S. PATENT DOCUMENTS

| | | | | |
|---|---|---|---|---|
| 918,570 | A | 4/1909 | Mather | 292/318 |
| 919,138 | A | 4/1909 | Drake et al. | 606/144 |
| 1,153,053 | A | 9/1915 | Forster | 43/44.85 |
| 1,565,041 | A | 12/1925 | Arneu | 24/129 R |
| 2,269,963 | A | 1/1942 | Wrapler | 604/604 |
| 2,286,578 | A | 6/1942 | Sauter | 606/144 |
| 2,485,531 | A | 10/1949 | Dzus et al. | 128/92 |
| 2,600,395 | A | 6/1952 | Domoj et al. | 87/13 |
| 3,143,916 | A | 8/1964 | Rice | 85/71 |
| 3,942,407 | A | 3/1976 | Mortensen | 85/71 |
| 3,946,740 | A | 3/1976 | Bassett | 128/334 |

(Continued)

FOREIGN PATENT DOCUMENTS

| | | | |
|---|---|---|---|
| DE | 025 32 242 | A1 | 2/1977 |
| DE | 042 35 602 | A1 | 4/1994 |

(Continued)

OTHER PUBLICATIONS

EP Partial European Search Report for EP02742470 3pgs, Apr. 13, 2004.

(Continued)

*Primary Examiner* — Tuan V Nguyen
(74) *Attorney, Agent, or Firm* — Matthew Scheele; Brian Szymezak

(57) ABSTRACT

Implant and delivery systems for soft tissue repair which affix soft tissue portions to a region of bone are described. Generally, the assembly includes two bone anchors preloaded through an inserter handle such that each anchor is penetrated into the bone directly. The first anchor is inserted through the tissue and into the bone, where it is locked into position. The first anchor has a suture or wire that protrudes through the tissue and threads through the second anchor and is secured to a rotatable suture reel located along the handle. The second anchor is inserted through the tissue and into the bone independently of the first anchor. Once the second anchor is deployed, the suture or wire is tensioned to secure the soft tissue to the bone and a suture plug within the second anchor is deployed to lock the suture or wire in place.

12 Claims, 28 Drawing Sheets

102
64'
54
74
32
30
64'
106
112
78
100
82
34

102
64'
54
74
30
32
64'
106
84
78
100
34
82

U.S. PATENT DOCUMENTS 3,994,521 A 11/1976 Van Gompel ................. 292/319
4,047,533 A 9/1977 Perciaccante et al. ..... 128/335.5
4,109,658 A 8/1978 Hughes ......................... 128/340
4,164,225 A 8/1979 Johnston et al. .............. 128/334
4,186,921 A 2/1980 Fox ................................ 29/461
4,210,148 A 7/1980 Stivala .......................... 606/232
4,274,324 A 6/1981 Giannuzzi ....................... 411/38
4,301,551 A 11/1981 Dore et al. ................... 623/13.3
4,319,428 A 3/1982 Fox .................................. 47/42
4,345,601 A 8/1982 Fukuda ......................... 128/339
4,373,530 A 2/1983 Kilejian ................... 128/334 R
4,384,389 A 5/1983 Sato .......................... 24/136 K
4,409,974 A 10/1983 Freedland ....................... 128/92
4,456,270 A 6/1984 Zettl et al. ....................... 279/62
4,467,478 A 8/1984 Jurgutis .......................... 606/75
4,483,023 A 11/1984 Hoffman, Jr. et al. ..... 623/13.15
4,493,323 A 1/1985 Albright et al. ............... 128/340
4,580,936 A 4/1986 Francis et al. .................. 411/38
4,590,928 A 5/1986 Hunt et al. ...................... 606/72
4,597,776 A 7/1986 Ullman et al. .............. 48/197 R
4,605,414 A 8/1986 Czajka ....................... 623/13.11
4,621,640 A 11/1986 Mulhollan et al. ............ 128/340
4,635,637 A 1/1987 Schreiber ...................... 128/337
4,657,461 A 4/1987 Smith .......................... 411/340
4,672,957 A 6/1987 Hourahane ..................... 606/80
4,680,835 A 7/1987 Horng ......................... 24/712.5
4,712,542 A 12/1987 Daniel et al. .................... 606/96
4,721,103 A 1/1988 Freedland ....................... 128/92
4,731,084 A 3/1988 Dunn et al. ................ 623/13.19
4,738,255 A 4/1988 Goble et al. .............. 128/92 YF
4,741,330 A 5/1988 Hayhurst .................... 123/43 R
4,750,492 A 6/1988 Jacobs .......................... 606/230
4,772,286 A 9/1988 Goble et al. ............... 623/13.14
4,779,616 A 10/1988 Johnson ........................ 606/148
4,781,182 A 11/1988 Purnell et al. ................... 128/92
4,792,336 A 12/1988 Hlavacek et al. .......... 623/13.18
4,809,408 A 3/1989 Abrahamson ............... 24/136 K
4,823,780 A 4/1989 Odensten et al. ............... 606/96
4,828,439 A 5/1989 Giannuzzi ....................... 411/37
4,834,755 A 5/1989 Silvestrini et al. ......... 623/13.19
4,836,205 A 6/1989 Barrett .......................... 128/340
4,851,005 A 7/1989 Hunt et al. ...................... 623/18
4,870,957 A 10/1989 Goble et al. .................... 606/73
4,917,700 A 4/1990 Aikins ....................... 623/13.19
4,923,461 A 5/1990 Caspari et al. ................ 606/146
4,926,860 A 5/1990 Stice et al. .................... 606/144
4,935,027 A 6/1990 Yoon ............................ 606/146
4,946,377 A 8/1990 Kovach ...................... 623/13.18
4,946,467 A 8/1990 Ohi et al. ...................... 606/228
4,946,468 A 8/1990 Li ................................ 606/232
4,957,498 A 9/1990 Caspari et al. ................ 606/146
4,962,929 A 10/1990 Melton, Jr. .................... 473/516
4,968,315 A 11/1990 Gatturna ......................... 606/72
4,981,149 A 1/1991 Yoon et al. .................... 128/898
4,987,665 A 1/1991 Dumican ........................ 28/218
5,002,550 A 3/1991 Li ................................ 606/139
5,019,093 A 5/1991 Kaplan et al. ................. 606/228
5,037,422 A 8/1991 Hayhurst ........................ 606/72
5,046,513 A 9/1991 Gatturna ....................... 128/898
5,059,201 A 10/1991 Asnis ........................... 606/144
5,062,344 A 11/1991 Gerker ............................... 87/8
5,085,661 A 2/1992 Moss ........................... 606/139
5,147,166 A 9/1992 Harker ........................... 411/29
5,195,542 A 3/1993 Gazielly et al. ................. 60/244
5,203,787 A 4/1993 Noblitt et al. ................. 606/232
RE34,293 E 6/1993 Goble et al. ............... 623/13.14
5,217,495 A 6/1993 Kaplan et al. .............. 623/13.18
5,219,359 A 6/1993 McQuilkin et al. ........... 606/232
5,222,977 A 6/1993 Esser ........................... 606/223
5,224,946 A 7/1993 Hayhurst ........................ 606/72
5,258,016 A 11/1993 DiPoto et al. ................. 606/232
5,259,846 A 11/1993 Granger et al. ............... 606/224
5,263,984 A 11/1993 Li ............................ 623/13.18
5,275,176 A 1/1994 Chandler ...................... 606/242
5,304,184 A 4/1994 Hathaway et al. ............ 606/144
5,306,290 A 4/1994 Martins et al. ................ 606/232
5,312,422 A 5/1994 Trott ............................ 606/144
5,318,575 A 6/1994 Chesterfield et al. ......... 606/151
5,324,308 A 6/1994 Pierce .......................... 606/232
5,326,205 A 7/1994 Anspach, Jr. et al. ........... 411/43
5,330,442 A 7/1994 Green .......................... 606/232
5,330,468 A 7/1994 Burkhart ......................... 606/96
5,330,488 A 7/1994 Goldrath ....................... 606/148
5,336,240 A 8/1994 Metzler ........................ 606/232
5,354,298 A 10/1994 Lee et al. ........................ 606/72
5,364,407 A 11/1994 Poll ............................. 606/139
5,376,118 A 12/1994 Kaplan et al. ............. 623/23.72
5,383,905 A 1/1995 Gold et al. ..................... 606/232
5,397,325 A 3/1995 Della Badia et al. ......... 606/144
5,405,352 A 4/1995 Weston ........................ 606/148
5,405,359 A 4/1995 Pierce .......................... 606/232
5,409,494 A 4/1995 Morgan .......................... 606/96
5,413,579 A 5/1995 Tom Du .......................... 606/87
5,417,691 A 5/1995 Hayhurst ........................ 606/72
5,417,699 A 5/1995 Klein et al. ................... 606/139
5,417,712 A 5/1995 Whitaker et al. ............. 606/232
5,431,666 A 7/1995 Sauer et al. ................... 606/139
5,441,508 A 8/1995 Gazielly et al. ............... 606/151
5,445,167 A 8/1995 Yoon et al. .................... 128/898
5,450,860 A 9/1995 O'Connor ..................... 606/224
5,454,823 A 10/1995 Richardson et al. .......... 606/148
5,464,427 A 11/1995 Curtis et al. .................. 606/232
5,470,335 A 11/1995 DuToit ........................... 606/73
5,472,452 A 12/1995 Trott ............................ 606/232
5,474,565 A 12/1995 Trott ............................ 606/144
5,480,403 A 1/1996 Lee et al. ........................ 606/72
5,486,197 A 1/1996 Le et al. ........................ 606/232
5,499,991 A 3/1996 Garman et al. ............... 606/148
5,501,683 A 3/1996 Trott .............................. 606/72
5,501,695 A 3/1996 Anspach, Jr. et al. ........... 606/72
5,505,735 A 4/1996 Li .................................. 606/72
5,514,159 A 5/1996 Matula et al. ................. 606/232
5,520,700 A * 5/1996 Beyar et al. ................... 606/139
5,522,820 A 6/1996 Caspari et al. ................ 606/148
5,527,322 A 6/1996 Klein et al. ................... 606/144
5,527,343 A 6/1996 Bonutti ......................... 606/232
5,531,792 A 7/1996 Huene ............................ 623/16
5,534,012 A 7/1996 Bonutti ......................... 606/232
5,540,703 A 7/1996 Barker, Jr. et al. ............ 606/139
5,545,180 A 8/1996 Le et al. ........................ 606/232
5,549,617 A 8/1996 Green et al. .................. 606/144
5,549,630 A 8/1996 Bonutti ......................... 606/232
5,553,360 A 9/1996 Lucas et al. ................. 24/136 K
5,562,689 A 10/1996 Green et al. .................. 606/151
5,569,305 A 10/1996 Bonutti ......................... 606/232
5,569,306 A 10/1996 Thal ............................. 606/232
5,571,104 A 11/1996 Li .................................. 606/72
5,571,120 A 11/1996 Yoon ............................ 606/148
5,573,540 A 11/1996 Yoon ............................ 606/139
5,573,542 A 11/1996 Stevens ......................... 606/144
5,573,548 A 11/1996 Nazre et al. ................... 606/232
5,575,801 A 11/1996 Habermeyer et al. .......... 606/148
5,584,835 A 12/1996 Greenfield ....................... 606/73
5,584,839 A 12/1996 Gieringer ........................ 606/96
5,584,860 A 12/1996 Goble et al. .................. 606/232
5,584,862 A 12/1996 Bonutti ......................... 606/232
5,591,207 A 1/1997 Coleman ....................... 606/232
5,593,189 A 1/1997 Little .............................. 289/17
5,601,558 A 2/1997 Torrie et al. ..................... 606/72
5,609,597 A 3/1997 Lehrer .......................... 606/139
5,611,801 A 3/1997 Songer ............................ 606/73
5,613,974 A 3/1997 Andreas et al. ............... 606/144
5,618,290 A 4/1997 Toy et al. ...................... 606/139
5,618,314 A 4/1997 Harwin et al. ................ 606/232
5,626,614 A 5/1997 Hart ............................. 606/232
5,630,824 A 5/1997 Hart ............................. 606/139
5,632,748 A 5/1997 Beck, Jr. et al. ................ 606/72
5,645,552 A 7/1997 Sherts .......................... 606/145
5,645,589 A 7/1997 Li .................................. 623/16
5,647,874 A 7/1997 Hayhurst ........................ 606/72
5,649,940 A 7/1997 Hart et al. ..................... 606/148
5,658,313 A 8/1997 Thal ............................. 606/232
5,665,108 A 9/1997 Galindo ........................ 606/215
5,665,110 A 9/1997 Chervitz et al. .............. 606/232
5,665,112 A 9/1997 Thal ............................. 606/232
5,667,528 A 9/1997 Colligan ....................... 606/224
D385,352 S 10/1997 Bales et al. .................. D24/145

5,681,333 A 10/1997 Burkhart et al. .............. 606/148
5,681,351 A 10/1997 Jamiolkowski et al. ...... 606/232
5,683,417 A 11/1997 Cooper ......................... 606/223
5,683,418 A 11/1997 Luscombe et al. ............ 606/232
5,683,419 A 11/1997 Thai ............................. 606/232
5,690,649 A 11/1997 Li ................................ 606/139
5,693,060 A 12/1997 Martin .......................... 606/148
5,697,950 A 12/1997 Fucci et al. ................... 606/232
5,702,397 A * 12/1997 Goble et al. .................. 606/232
5,702,398 A 12/1997 Tarabishy
5,707,362 A 1/1998 Yoon ............................ 604/164
5,707,394 A 1/1998 Miller et al. .................. 606/232
5,709,708 A 1/1998 Thal ............................. 606/232
5,720,765 A 2/1998 Thal ............................. 606/232
5,725,529 A 3/1998 Nicholson et al. .............. 606/72
5,725,541 A 3/1998 Anspach, III et al. ........ 606/151
5,728,136 A 3/1998 Thal ............................. 606/232
5,733,307 A 3/1998 Dinsdale ....................... 606/232
5,741,281 A 4/1998 Martin .......................... 606/148
5,741,282 A 4/1998 Anspach, III et al. ........ 606/151
5,766,250 A 6/1998 Chervitz et al. ................ 623/13
5,776,150 A 7/1998 Nolan et al. .................. 606/148
5,779,719 A 7/1998 Klein et al. ................... 606/144
5,782,863 A 7/1998 Bartlett ......................... 606/232
5,782,864 A 7/1998 Lizardi ......................... 606/232
5,782,865 A 7/1998 Grotz .............................. 606/72
5,791,899 A 8/1998 Sachdeva ...................... 433/173
5,792,152 A 8/1998 Klein et al. ................... 606/144
5,792,153 A 8/1998 Swain et al. .................. 606/144
5,797,927 A 8/1998 Yoon ............................ 606/144
5,797,963 A 8/1998 McDevitt ...................... 606/232
5,810,848 A 9/1998 Hayhurst ...................... 606/144
5,810,854 A 9/1998 Beach ........................... 606/232
5,814,052 A 9/1998 Nakao et al. .................. 606/148
5,814,056 A 9/1998 Prosst et al. .................. 606/151
5,814,071 A 9/1998 McDevitt ...................... 606/232
5,814,072 A 9/1998 Bonutti ......................... 606/232
5,843,111 A 12/1998 Vijfvinkel ..................... 606/171
5,849,004 A 12/1998 Bramlet ........................ 606/232
5,860,978 A 1/1999 McDevitt ........................ 606/72
5,860,991 A 1/1999 Klein et al. ................... 606/144
5,860,992 A 1/1999 Daniel et al. .................. 606/145
5,868,789 A 2/1999 Heubner ....................... 606/232
5,879,372 A 3/1999 Bartlett ......................... 606/232
5,882,340 A 3/1999 Yoon ............................ 604/164
5,885,294 A 3/1999 Pedlick et al. .................. 606/80
5,891,168 A 4/1999 Thal ............................. 606/232
5,893,850 A 4/1999 Cachia ............................ 606/72
5,902,311 A 5/1999 Andreas et al. ............... 606/144
5,904,692 A 5/1999 Steckel et al. ................ 606/139
5,911,721 A 6/1999 Nicholson et al. .............. 606/72
5,921,994 A 7/1999 Andreas et al. ............... 606/144
5,935,107 A 8/1999 Taylor et al. .................. 604/164
5,935,129 A 8/1999 Mdevitt ........................... 606/72
5,941,900 A 8/1999 Bonutti ......................... 606/232
5,941,901 A 8/1999 Egan ............................ 606/232
5,944,724 A 8/1999 Lizardi ......................... 606/104
5,944,739 A 8/1999 Zlock et al. ................... 606/232
5,947,982 A 9/1999 Duran .......................... 606/139
5,948,000 A 9/1999 Larsen et al. ................. 606/232
5,948,001 A 9/1999 Larsen .......................... 606/232
5,948,002 A 9/1999 Bonutti ......................... 606/232
5,957,953 A 9/1999 DiPoto et al. ................. 606/232
5,957,968 A 9/1999 Belden et al. ................. 607/126
5,961,530 A 10/1999 Moore et al. .................. 606/148
5,961,538 A 10/1999 Pedlick et al. ................ 606/232
5,968,044 A 10/1999 Nicholson et al. .............. 606/72
5,980,558 A 11/1999 Wiley ........................... 606/232
5,980,559 A 11/1999 Bonutti ......................... 606/232
5,984,933 A 11/1999 Yoon ............................ 606/148
5,993,459 A 11/1999 Larsen .......................... 606/104
6,001,104 A 12/1999 Benderev et al. ............... 606/80
6,001,109 A 12/1999 Kontos .......................... 606/148
6,007,566 A 12/1999 Wenstrom ..................... 606/232
6,007,567 A 12/1999 Bonutti ......................... 606/232
6,010,525 A 1/2000 Bonutti et al. ................ 606/232
6,013,083 A 1/2000 Bennett ......................... 606/104
6,017,346 A 1/2000 Grotz .............................. 606/72
6,022,360 A 2/2000 Reimels et al. ............... 606/144
6,022,373 A 2/2000 Li ................................ 606/232
6,024,758 A 2/2000 Thal ............................. 606/232
6,033,430 A 3/2000 Bonutti ......................... 606/232
6,036,699 A 3/2000 Andreas et al. ............... 606/139
6,045,571 A 4/2000 Hill et al. ...................... 606/228
6,045,572 A 4/2000 Johnson et al. ............... 606/232
6,045,573 A 4/2000 Wenstrom et al. ............ 606/232
6,045,574 A 4/2000 Thal ............................. 606/232
6,048,351 A 4/2000 Gordon et al. ................ 606/144
6,051,006 A 4/2000 Shluzas et al. ................ 606/148
6,053,935 A 4/2000 Brenneman et al. .......... 606/232
6,056,773 A 5/2000 Bonutti ......................... 606/232
6,066,146 A 5/2000 Carroll et al. ................ 606/148
6,068,648 A 5/2000 Cole et al. ..................... 606/232
6,083,243 A 7/2000 Pokropinski et al. ......... 606/230
6,086,608 A 7/2000 Elk et al. ....................... 606/232
6,096,051 A 8/2000 Kortenbach et al. .......... 606/144
6,102,934 A 8/2000 Li ................................ 606/232
6,117,160 A 9/2000 Bonutti ......................... 606/215
6,117,161 A 9/2000 Li ................................ 606/232
6,143,004 A 11/2000 Davis et al. ................... 606/144
6,146,386 A 11/2000 Blackman ..................... 606/103
6,146,406 A 11/2000 Shluzas et al. ................ 606/232
6,149,669 A 11/2000 Li ................................ 606/232
6,156,039 A 12/2000 Thal ............................... 606/72
6,156,056 A 12/2000 Kearns et al. ................ 606/232
6,159,235 A 12/2000 Kim ............................. 606/232
6,162,537 A 12/2000 Martin et al. ................. 428/373
6,165,204 A 12/2000 Levinson et al. ............. 606/232
6,171,317 B1 1/2001 Jackson et al. ............... 606/148
6,174,324 B1 1/2001 Egan et al. .................... 606/232
6,200,329 B1 3/2001 Fung et al. .................... 606/232
6,200,893 B1 3/2001 Sneh ............................ 438/685
6,206,895 B1 3/2001 Levinson ...................... 606/144
6,214,028 B1 4/2001 Yoon et al. .................... 606/205
6,217,592 B1 4/2001 Freda et al. ................... 606/145
6,228,096 B1 5/2001 Marchand ..................... 606/139
6,241,736 B1 6/2001 Sater ............................ 606/104
6,267,766 B1 7/2001 Burkhart ......................... 606/72
6,280,474 B1 8/2001 Cassidy et al. ............. 623/16.11
6,293,961 B2 9/2001 Schwartz ...................... 606/232
6,315,781 B1 11/2001 Reinhardt ..................... 606/108
6,319,252 B1 11/2001 McDevitt et al. ............... 606/60
6,319,269 B1 11/2001 Li ................................ 606/232
6,319,271 B1 11/2001 Schwartz et al. ............. 606/232
6,328,758 B1 12/2001 Tornier et al. ................ 606/232
6,355,053 B1 3/2002 Li ................................ 606/232
6,409,743 B1 6/2002 Fenton .......................... 606/232
6,432,123 B2 8/2002 Schwartz et al. ............. 606/232
6,436,109 B1 8/2002 Konts ........................... 606/148
6,451,030 B2 9/2002 Li et al. ........................ 606/139
6,464,713 B2 10/2002 Bonutti ......................... 606/232
6,468,293 B2 10/2002 Bonutti et al. ................ 606/232
6,471,715 B1 10/2002 Weiss ........................... 606/216
6,475,230 B1 11/2002 Bonutti et al. ................ 606/232
6,491,714 B1 12/2002 Bennett ......................... 606/232
6,517,542 B1 2/2003 Papay et al. ..................... 606/73
6,520,980 B1 2/2003 Foerster ....................... 606/232
6,524,317 B1 2/2003 Ritchart et al. ................. 606/72
6,527,794 B1 3/2003 McDevitt et al. ............. 606/232
6,533,796 B1 3/2003 Sauer et al. .................. 606/144
6,540,770 B1 4/2003 Tornier et al. ................ 606/232
6,547,800 B2 4/2003 Foerster et al. ............... 606/151
6,551,330 B1 4/2003 Bain et al. .................... 606/144
6,569,187 B1 5/2003 Bonutti et al. ................ 606/232
6,575,987 B2 6/2003 Appell et al. ................. 606/151
6,582,453 B1 6/2003 Tran et al. .................... 606/232
6,585,730 B1 7/2003 Foerster ....................... 606/232
6,635,073 B2 10/2003 Bonutti ......................... 606/232
6,638,279 B2 10/2003 Bonutti ........................... 606/60
6,645,227 B2 11/2003 Fallin et al. .................. 606/232
6,648,903 B1 11/2003 Pierson, III .................. 606/232
6,652,561 B1 11/2003 Tran ............................ 606/232
6,656,183 B2 12/2003 Colleran et al. .............. 606/232
6,660,008 B1 12/2003 Foerster et al. ................. 606/72
6,660,023 B2 12/2003 McDevitt et al. ............. 606/232
6,679,896 B2 1/2004 Gellman et al. ............. 606/148
6,682,549 B2 1/2004 Bartlett ......................... 606/232
6,689,154 B2 2/2004 Bartlett ......................... 606/232

| | | | | |
|---|---|---|---|---|
| 6,692,516 | B2 | 2/2004 | West et al. | 606/232 |
| 6,712,830 | B2 | 3/2004 | Esplin | 606/152 |
| 6,716,234 | B2 | 4/2004 | Grafton | 606/228 |
| 6,736,829 | B1 | 5/2004 | Li et al. | 606/232 |
| 6,770,076 | B2 | 8/2004 | Foerster | 606/72 |
| 6,780,198 | B1 | 8/2004 | Gregoire et al. | 606/232 |
| 6,855,157 | B2 | 2/2005 | Foerster et al. | 606/232 |
| 6,860,887 | B1 | 3/2005 | Frankle | 606/104 |
| 6,939,379 | B2 | 9/2005 | Sklar | 623/13.14 |
| 6,972,027 | B2 | 12/2005 | Fallin et al. | 606/232 |
| 7,029,490 | B2 | 4/2006 | Grafton | 606/228 |
| 7,083,638 | B2 | 8/2006 | Foerster | 606/232 |
| 7,087,064 | B1 | 8/2006 | Hyde | 606/142 |
| 7,090,690 | B2 * | 8/2006 | Foerster et al. | 606/232 |
| 7,104,999 | B2 | 9/2006 | Overaker | 606/142 |
| 7,150,750 | B2 | 12/2006 | Damarati | 623/17.11 |
| 7,247,164 | B1 | 7/2007 | Ritchart et al. | 606/232 |
| 7,320,701 | B2 * | 1/2008 | Haut et al. | 606/232 |
| 7,329,272 | B2 | 2/2008 | Burkhart et al. | 606/232 |
| 7,410,489 | B2 | 8/2008 | Dakin et al. | 606/103 |
| 7,527,590 | B2 | 5/2009 | Suzuki et al. | 600/104 |
| 7,556,640 | B2 | 7/2009 | Foerster | 606/232 |
| 7,588,587 | B2 | 9/2009 | Barbieri et al. | 606/232 |
| 7,615,061 | B2 | 11/2009 | White et al. | 606/148 |
| 7,637,926 | B2 | 12/2009 | Foerster et al. | 606/232 |
| 7,674,274 | B2 | 3/2010 | Foerster et al. | 606/232 |
| 7,682,374 | B2 | 3/2010 | Foerster | 606/72 |
| 7,695,494 | B2 | 4/2010 | Foerster | 606/72 |
| 7,806,909 | B2 | 10/2010 | Fallin et al. | 606/232 |
| 7,837,710 | B2 | 11/2010 | Lombardo et al. | 606/232 |
| 7,963,972 | B2 * | 6/2011 | Foerster et al. | 606/139 |
| 8,105,343 | B2 | 1/2012 | White et al. | 606/144 |
| 8,105,355 | B2 | 1/2012 | Page et al. | 606/232 |
| 8,109,966 | B2 | 2/2012 | Ritchart et al. | 606/232 |
| 8,133,258 | B2 | 3/2012 | Foerster et al. | 606/232 |
| 2003/0167062 | A1 | 9/2003 | Gambale | 606/232 |
| 2003/0195563 | A1 | 10/2003 | Foerster | 606/232 |
| 2003/0195564 | A1 | 10/2003 | Tran et al. | 606/232 |
| 2004/0138683 | A1 * | 7/2004 | Shelton et al. | 606/151 |
| 2004/0138706 | A1 | 7/2004 | Abrams et al. | 606/232 |
| 2004/0153074 | A1 * | 8/2004 | Bojarski et al. | 606/72 |
| 2004/0236336 | A1 | 11/2004 | Foerster et al. | 606/72 |
| 2005/0033364 | A1 | 2/2005 | Gregoire et al. | 606/232 |
| 2005/0080455 | A1 | 4/2005 | Schmieding et al. | 606/232 |
| 2005/0090827 | A1 | 4/2005 | Gedebou | 606/72 |
| 2005/0277986 | A1 | 12/2005 | Foerster et al. | 606/232 |
| 2006/0004364 | A1 | 1/2006 | Green et al. | 606/72 |
| 2006/0074422 | A1 | 4/2006 | Story et al. | 606/142 |
| 2006/0079904 | A1 * | 4/2006 | Thal | 606/72 |
| 2006/0106422 | A1 * | 5/2006 | Del Rio et al. | 606/232 |
| 2006/0161159 | A1 | 7/2006 | Dreyfuss et al. | 606/72 |
| 2006/0161183 | A1 | 7/2006 | Sauer | 606/148 |
| 2006/0259076 | A1 * | 11/2006 | Burkhart et al. | 606/228 |
| 2006/0271060 | A1 | 11/2006 | Gordon | 606/232 |
| 2006/0271105 | A1 | 11/2006 | Foerster et al. | 606/232 |
| 2007/0135843 | A1 * | 6/2007 | Burkhart | 606/232 |
| 2007/0142838 | A1 | 6/2007 | Jordan | 606/75 |
| 2008/0015594 | A1 | 1/2008 | Ritchart et al. | 606/72 |
| 2008/0051836 | A1 | 2/2008 | Foerster et al. | 606/232 |
| 2008/0154286 | A1 | 6/2008 | Abbott et al. | 606/139 |
| 2008/0319478 | A1 | 12/2008 | Foerster et al. | 606/148 |
| 2009/0048613 | A1 | 2/2009 | Surti | 606/139 |
| 2009/0069823 | A1 | 3/2009 | Foerster et al. | 606/103 |
| 2009/0222040 | A1 | 9/2009 | Foerster et al. | 606/232 |
| 2009/0222041 | A1 | 9/2009 | Foerster et al. | 606/232 |
| 2010/0191283 | A1 | 7/2010 | Foerster et al. | 606/232 |
| 2012/0095507 | A1 | 4/2012 | White et al. | 606/232 |
| 2012/0158052 | A1 | 6/2012 | Foerster et al. | 606/232 |

FOREIGN PATENT DOCUMENTS

| | | | |
|---|---|---|---|
| DE | 196 28 909 | A1 | 1/1998 |
| EP | 0 535 906 | A2 | 4/1993 |
| EP | 0 571 686 | A1 | 12/1993 |
| EP | 0 611557 | A2 | 8/1994 |
| EP | 1 072 234 | A2 | 1/2001 |
| EP | 1 072 237 | A1 | 1/2001 |
| EP | 1987779 | | 11/2008 |
| FR | 2777442 | | 10/1999 |
| FR | 2777447 | | 10/1999 |
| GB | 2452825 | | 3/2009 |
| JP | 2286468 | | 11/1990 |
| JP | 8-52154 | | 2/1996 |
| JP | 08-206121 | | 8/1996 |
| JP | 11-502437 | | 3/1999 |
| JP | 2000-225118 | | 8/2000 |
| WO | 91/06247 | | 5/1991 |
| WO | 95/06439 | | 3/1995 |
| WO | 95/25469 | | 9/1995 |
| WO | 96/17544 | | 6/1996 |
| WO | 96/28118 | | 9/1996 |
| WO | 97/20522 | | 6/1997 |
| WO | 98/07374 | | 2/1998 |
| WO | 99/22648 | | 5/1999 |
| WO | 99/53843 | | 10/1999 |
| WO | 99/53844 | | 10/1999 |
| WO | 02/21997 | | 3/2002 |
| WO | 03/049620 | | 6/2003 |
| WO | 03/090627 | | 11/2003 |
| WO | 2004/082724 | | 9/2004 |
| WO | 2008/022250 | | 2/2008 |
| WO | 2009/032695 | | 3/2009 |
| WO | 2009/114811 | | 9/2009 |

OTHER PUBLICATIONS

EP Supplementary European Search Report for EP02742470 5pgs, Jul. 30, 2004.
European Search Report for EP02791363 4pgs, Mailed Mar. 5, 2007.
EP Extended Search Report for EP09162639 4pgs, Oct. 28, 2009.
EP Supplementary European Search Report for EP02792506 3pgs; Mar. 24, 2010.
PCT International Preliminary Examination Report for PCT/US01/17689 15pgs, Feb. 9, 2003.
PCT International Preliminary Examination Report for PCT/US01/21905 3pgs, Oct. 17, 2003.
PCT International Preliminary Examination Report for PCT/US02/04231 3pgs, Nov. 13, 2002.
PCT International Preliminary Examination Report for PCT/US02/17493 4pgs, Sep. 8, 2003.
PCT International Preliminary Examination Report for PCT/US02/38632 3 pgs, Jul. 23, 2004.
PCT International Preliminary Examination Report for PCT/US02/41018 3pgs, Feb. 22, 2004.
PCT International Preliminary Examination Report for PCT/US03/35695 4pgs, Dec. 21, 2005.
PCT International Search Report for PCT/US01/17689 3pgs, Mailed Dec. 19, 2001.
PCT International Search Report for PCT/US01/21905 3pgs, Mailed Jan. 22, 2002.
PCT International Search Report for PCT/US02/04231 1pg, Mailed Aug. 14, 2002.
PCT International Search Report for PCT/US02/17493 1pg, Mailed Mar. 27, 2003.
PCT International Search Report for PCT/US02/38632 2 pgs, Mailed May 16, 2003.
PCT International Search Report for PCT/US02/41018 2pgs, Mailed Jun. 5, 2003.
PCT International Search Report for PCT/US03/35695 1 pg, Mailed Feb. 14, 2005.
PCT Search Report for PCT/US06/20657 1pg Mailed Oct. 2, 2007.
PCT Written Opinion for PCT/US06/20657 4pgs, Mailed Oct. 2, 2007.
PCT Search Report and Written Opinion for PCT/US06/21125 6pgs, Mailed May 22, 2008.
UK Search Report for GB 0816111.9 3pgs, Dec. 16, 2008.
UK Search Report for GB 0911011.5 4pgs, Oct. 27, 2009.
UK Search Report for GB 0911013.1 4pgs, Oct. 27, 2009.
UK Search and Examination Report for GB 0911011.5 2pgs, May 28, 2012.

* cited by examiner

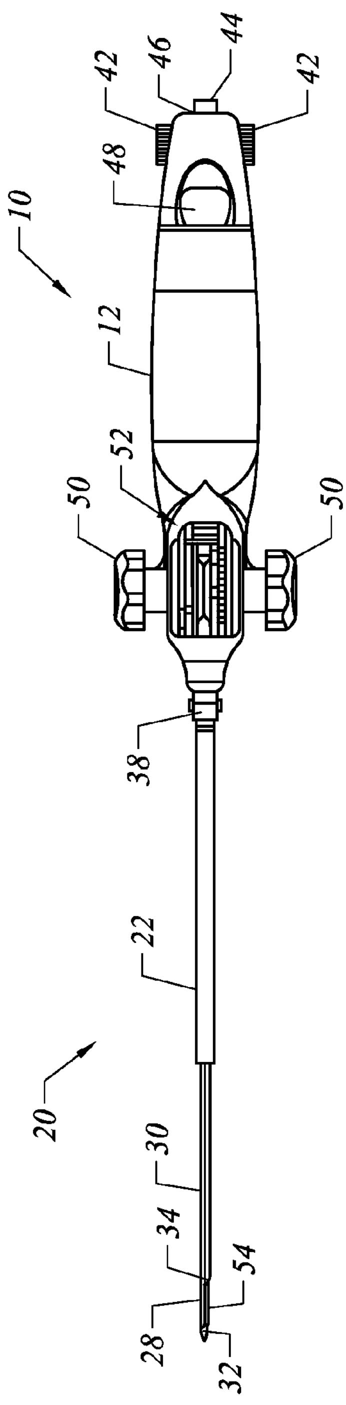
FIG. 1A
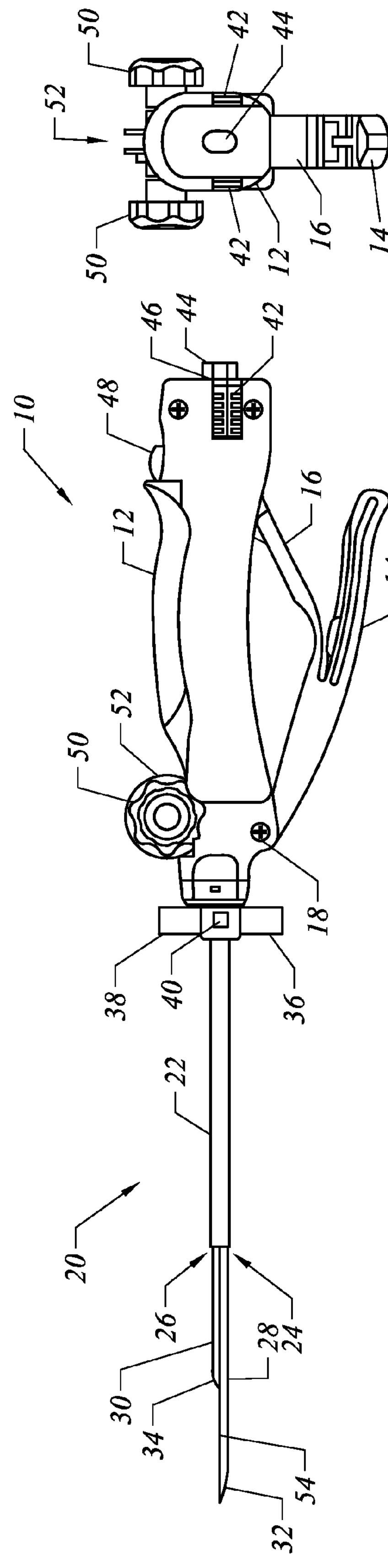
FIG. 1B
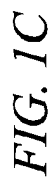

IMPLANT AND DELIVERY SYSTEM FOR SOFT TISSUE REPAIR

CROSS REFERENCE TO RELATED APPLICATIONS

This application is a divisional of U.S. application Ser.No. 11/854,235, filed Sep. 12, 2007, now U.S. Pat. No. 7,963,972, the complete disclosure of which is incorporated herein by reference for all purposes.

FIELD OF THE INVENTION

The present invention relates to apparatus and methods for repairing soft tissue regions. More particularly, the present invention relates to apparatus and methods for adjustably affixing torn soft tissues to a region of bone.

BACKGROUND OF THE INVENTION

A significant number of surgical patients who are diagnosed with a torn rotator cuff typically present in the operating room with a cuff that is only partially torn on the articular side of the tendon. Rather than being avulsed from the bone in a way that allows the surgeon to access the torn edge for suture placement and eventual re-attachment to the bone, these partial tears are characterized by torn tendon fibers on the articular side of the tendon and intact tendon fibers on the bursal side of the tendon. These tears have been given the label of PASTA tears (Partial Articular Supraspinatus Tendon Avulsion).

The surgeon typically assesses a rotator cuff tear by placing an arthroscope in the joint capsule and visualizing both the articular and bursal side of the tendon. The footprint of the supraspinatus tendon (one of the four tendons that comprise the rotator cuff and the most common tendon to tear) on the humeral head is typically about 1 cm in length medial to lateral and 2 to 3 cm in width anterior to posterior. When the surgeon visualizes a tear on the articular side that is not reflected entirely through the tendon footprint to the bursal side, the surgeon typically estimates the depth of the tear. If the tear is less than 5 mm (or less than roughly 50% of the tendon thickness), the typical approach is to debride the underside of the tendon while leaving the rest of the tendon alone.

If the surgeon determines that the avulsion is greater than 50% of the tendon, there are usually two possible approaches to the repair. The first approach is to complete the tear by cutting the tendon off from the bone to create a complete tear of the tendon and to proceed with a conventional arthroscopic rotator cuff repair. The second approach is to repair the tendon by inserting anchors trans-tendon into the underlying bone, passing sutures through the tendon, and then tying the tendon down.

The first approach may be a technically easier procedure to perform and many surgeons may feel that they can create a better ultimate repair by using this technique. However, this approach requires a surgeon to cut away viable tendon in order to subsequently repair it. The second approach of inserting anchors trans-tendon may be considered a more reasonable approach. However, this approach is difficult and requires a very high level of surgical skill to accomplish. Moreover, this approach also raises concerns about the size of the holes created in the tendon to place screw-type bone anchors (typically 3 to 5 mm in diameter) through the tendon and whether these holes may compromise the repair.

BRIEF SUMMARY OF THE INVENTION

Therefore, a need has arisen for devices and methods which facilitate trans-tendon soft tissue repairs with minimal insult to the tendon.

In repairing soft tissue, such as a tendon of a torn rotator cuff to a region of bone such as the humeral head, the anchor inserter assembly may generally allow the user to insert at least two anchors into bone independently of one another, lock each anchor into the bone, allow the user to subsequently tension a length of suture or wire between the anchors to affix the soft tissue, immobilize the suture or wire, and then disassociate the inserter assembly from the anchors, leaving them and the affixed soft tissue behind in the bone. Generally, the anchor inserter assembly may include the two bone anchors preloaded through an inserter handle having two independently operating inserter shafts. Both anchors may include a robust tip (e.g., 316L implant grade stainless steel) welded or otherwise coupled onto a hypotube (e.g., also 316L stainless steel) such that each anchor may be penetrated into the bone directly without the need of a bone drill, drill guide, or pathfinder.

The first of the two bone anchors may be inserted through the soft tissue and pounded or otherwise implanted into the bone, where the anchor may be locked into position and the support sleeve is retracted. The primary bone anchor may have an internally secured suture or wire end that protrudes through the tissue and threads through the secondary anchor and is secured to rotatable suture reel located along the handle. The secondary bone anchor may also be inserted through the tissue and pounded or otherwise implanted into the bone a distance from the primary bone anchor to create a suture bridge across the soft tissue to be repaired. Once the secondary bone anchor has been deployed, the suture or wire may be tensioned to secure the soft tissue to the bone and a suture plug within the secondary anchor may be deployed to lock the suture or wire and the secondary support sleeve may be retracted.

The primary anchor may be inserted through a first portion of the soft tissue to be repaired and brought into contact against the underlying bone region. With the piercing tip of the primary anchor contacting the bone, the primary sleeve lock tab may be removed to release the primary support sleeve to slide proximally relative to the primary anchor. A proximal end of the inserter handle may be tapped, e.g., by using a mallet, to drive the primary anchor into the bone as the primary support sleeve remains above the bone surface. An anchor depth indicator may be located along the driver at a distance from a distal end of the driver proximal to the anchor. A depth indicator may also be visible through the window along the barrel support to indicate to the user when the primary anchor has been driven an appropriate depth into the bone.

With the primary anchor suitably implanted, the anchor wings may be deployed within the bone by actuating the hand lever once to lock a position of the anchor and to prevent or inhibit the primary anchor from being pulled out of the bone. A function switch may be depressed and the hand lever actuated again to release the primary anchor from the driver. Following the primary anchor deployment, a primary driver block and primary support sleeve may be removed entirely from the inserter assembly to allow for placement and implantation of a secondary anchor into the tissue.

The secondary anchor may be positioned at a second region of tissue by passing the secondary anchor through the tissue and into contact against the underlying bone. The anchors are desirably placed at a distance from one another as determined by the surgeon as appropriate for the surgical repair. A damaged or torn region of the tissue to be repaired may be positioned between where the anchors are implanted. Once the secondary anchor has been suitably positioned through the tissue and along the bone, the secondary sleeve lock tab may be removed to release the secondary support sleeve to slide proximally relative to the secondary anchor. Similar to the implantation of the primary anchor, a proximal end of the inserter handle may be tapped, e.g., by using a mallet, to drive the secondary anchor into the bone until the anchor depth indicator has been reached as the secondary support sleeve remains above the bone surface.

Once the secondary anchor has been implanted into the bone to a suitable depth, the anchor wings may be deployed along the secondary anchor to lock the anchor in place within the bone by actuating the hand lever once on the handle. With both anchors now implanted through the tissue and within bone, the length of suture or wire may be tensioned through the anchors. Once suture or wire has been desirably tensioned, a suture plug may be urged into a desired position (such as by retracted the suture plug proximally through the secondary anchor by depressing the hand lever a second time until the suture plug is pulled into a compression zone) such that the suture or wire is locked relative to the anchors. With the suture or wire maintained in a tensioned state between the anchors, the secondary anchor may be released from the driver. The length of the suture or wire proximal to the second anchor may be trimmed to complete the procedure and leave the implanted anchors and tensioned suture or wire within the bone and repaired soft tissue.

BRIEF DESCRIPTION OF THE DRAWINGS

FIGS. 1A to 1C show top, side, and end views, respectively, of a variation of an anchor inserter assembly;

DETAILED DESCRIPTION OF THE INVENTION

Figure 2A:
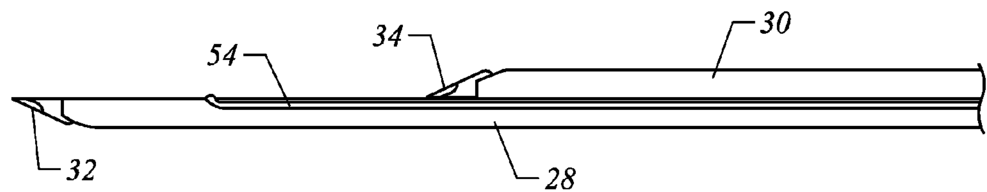
FIGS. 2A and 2B show side and perspective views, respectively, of the primary and secondary anchors positioned within their respective support sleeves.

In repairing soft tissue by anchoring the soft tissue (such as a tendon of a torn rotator cuff) to a region of bone, the anchor inserter assembly may generally allow the user to insert at least two anchors into bone independently of one another, lock each anchor into the bone, allow the user to subsequently tension a length of suture or wire between the anchors to affix the soft tissue, immobilize the suture or wire, and then disassociate the inserter assembly from the anchors, leaving them and the affixed soft tissue behind in the bone. In particular, such an anchor inserter assembly may preferably eliminate the need to separately pass suture or wire, eliminate the need to tie knots, allow the procedure to be performed without the need to move an arthroscope from an articular side to a bursal side of the cuff, and by virtue of the small diameter of the anchor implants, reduce the size of the hole placed in the cuff when passing the implant through.

Generally, the anchor inserter assembly described herein may include two bone anchors preloaded through an inserter handle having two independently operating inserter shafts. Both anchors may include a robust tip (e.g., 316L implant grade stainless steel) welded or otherwise coupled onto a hypotube (e.g., also 316L stainless steel) such that each anchor may penetrate into the bone directly without the need of a bone drill, drill guide, or pathfinder. The first of the two bone anchors may be inserted through the soft tissue and pounded or otherwise implanted into the bone as the support sleeve is retracted, where the anchor may be locked into position. The primary bone anchor may have an internally secured suture or wire end that protrudes through the tissue and threads through the secondary anchor and is secured to a rotatable suture reel located along the handle. The secondary bone anchor may also be selectively inserted through the tissue and pounded or otherwise implanted into the bone as the support sleeve is retracted at a distance from the primary bone anchor to create a suture bridge across the soft tissue to be repaired. Once the secondary bone anchor has been deployed, the suture or wire may be tensioned to secure the soft tissue to the bone and a suture plug within the secondary anchor may be deployed to lock the suture or wire.

Turning now to FIGS. 1A, 1B, and 1C, top, side, and end views, respectively, of one variation of anchor inserter assembly 10 is illustrated where a barrel assembly 20 may be seen coupled to and extending from handle 12. The various components of anchor inserter assembly 10 are first described generally but each component will be described in further detail herein below. Handle 12 may include hand lever 14 rotatingly attached to handle 12 via pivot 18 with lever 16 extending from hand lever 14 into mechanical attachment within handle 12, as described in further detail below. Barrel assembly 20 extends from handle 12 and comprises barrel support 22 which defines at least one common lumen therethrough in one variation and a primary barrel lumen 24 and secondary barrel lumen 26 in another variation, as shown. Primary support sleeve 28 may slidingly extend through primary barrel lumen 24 to house primary anchor 32 within or at a distal end of primary support sleeve 28, as shown. Likewise, secondary support sleeve 30 may extend through secondary barrel lumen 26 to house secondary anchor 34 within or at a distal end of secondary support sleeve 30.

In one variation as shown, secondary support sleeve 30 may have a length which is relatively shorter than a length of primary support sleeve 28 such that secondary anchor 34 is positioned proximally of primary anchor 32 to provide sufficient clearance for insertion of the respective anchors into the tissue regions to be prepared without interference from one another. Yet in other variations, both support sleeves 28, 30 may be configured to have substantially equivalent lengths such that when both anchors 32, 34 are positioned within their respective support sleeves, they may be directly adjacent to one another. In such a case, during anchor insertion into the bone, each support sleeve may be inserted into and/or removed from the inserter assembly separately from one another to provide sufficient clearance.

In either case, anchor inserter assembly 10 may also include primary sleeve lock tab 36 and secondary sleeve lock tab 38 positioned along both sides of barrel support 22. Each lock tab 36, 38 may be removably inserted along barrel support 22 to lock a position of each respective primary and secondary support sleeve 28, 30 to inhibit or prevent premature sliding of the sleeves proximally through barrel support 22 during an anchor insertion procedure. Moreover, upon removal from barrel support 22, each lock 36, 38 may reveal a visual indication through window 40 of anchor insertion depth when driven into the underlying bone, as described in further detail below.

Within handle 12, primary driver block 44 and secondary driver block 46 may be slidably disposed to control the advancement and/or retraction of their respective support sleeves 28, 30 and anchors 32, 34 as controlled by the actuation of hand lever 14 and lever 16 during a procedure. The actuation of a particular driver block and deployment of an anchor may be controlled not only by the articulation of lever 16 but also the depression of function switch 48 also located on handle 12. Moreover, primary driver block 44 may be removed from handle 12 by depressing or squeezing upon primary anchor removal tabs 42 to release primary driver block 44 to allow for the deployment of secondary anchor 34 into the bone without interference from primary support sleeve 28.

With both anchors 32, 34 positioned within their respective support sleeves 28, 30 for deployment, a length of suture or wire 54 is affixed to primary anchor 32 and may slidingly pass through secondary anchor 34 to allow for the implantation of each anchor independently of one another while maintaining the interconnection between the two during and after deployment. Once both anchors have been implanted within the bone, the length of suture or wire 54 extending between the two anchors may be subsequently tightened or cinched with respect to one another via turning or actuating one or more suture reel control knobs 50 connected to suture reel 52 (as also shown in FIG. 3), which in turn is attached to the suture or wire 54 and is configured to tension the length such that the soft tissue bridged between the implanted anchors by suture or wire 54 are tightened and affixed to the underlying bone.

Figure 2B:
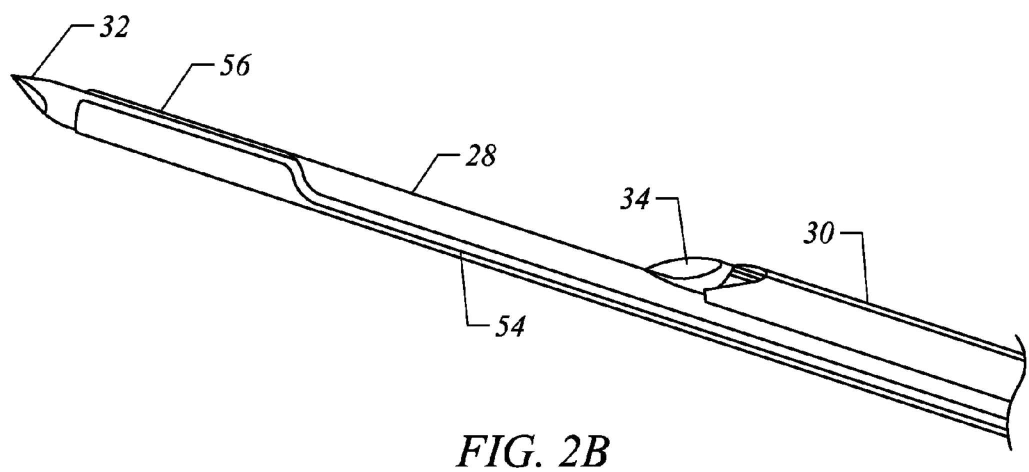

FIGS. 2A and 2B show side and perspective views, respectively, of the primary and secondary anchors 32, 34 positioned within their respective support sleeves 28, 30. As seen, the piercing tips of each anchor 32, 34 are exposed beyond the distal ends of each support sleeve 28, 30 while primary support sleeve 28 may also define slot 56 having a length along a distal end of primary support sleeve 28 coincident with a length of primary anchor 32 to allow for passage of suture or wire 54 from primary anchor 32 to secondary anchor 34. The interconnecting length of suture or wire 54 may comprise various sutures or wires suitable for soft tissue repair, such as braided #2 MagnumWire® suture (Arthrocare Corporation, Austin, Tex.).

Figure 3:
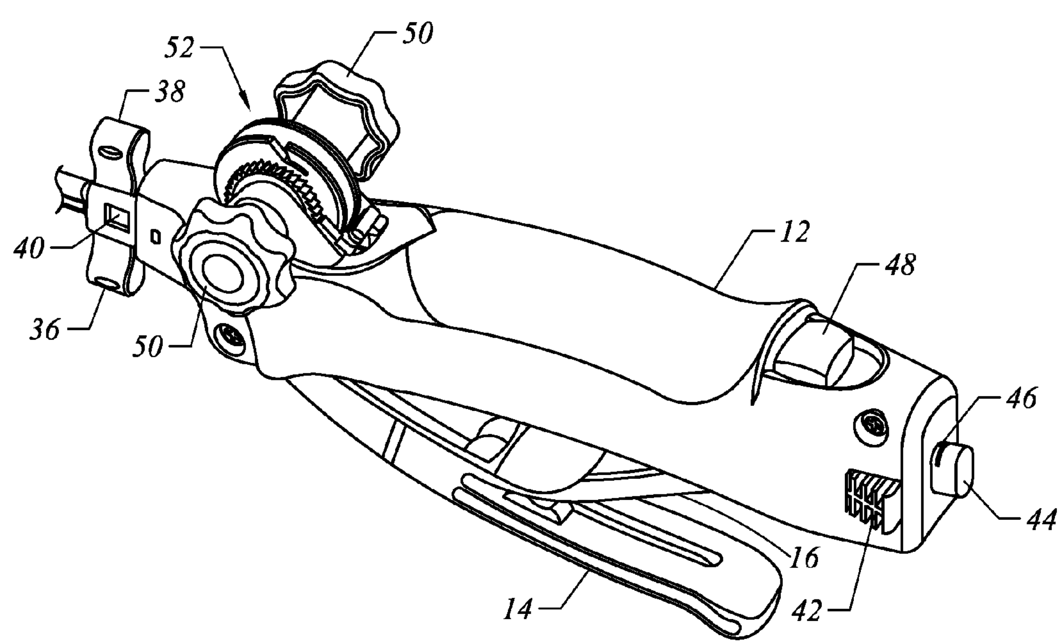
FIG. 3 shows a perspective view of a handle assembly of the anchor inserter assembly.
Figure 4A:
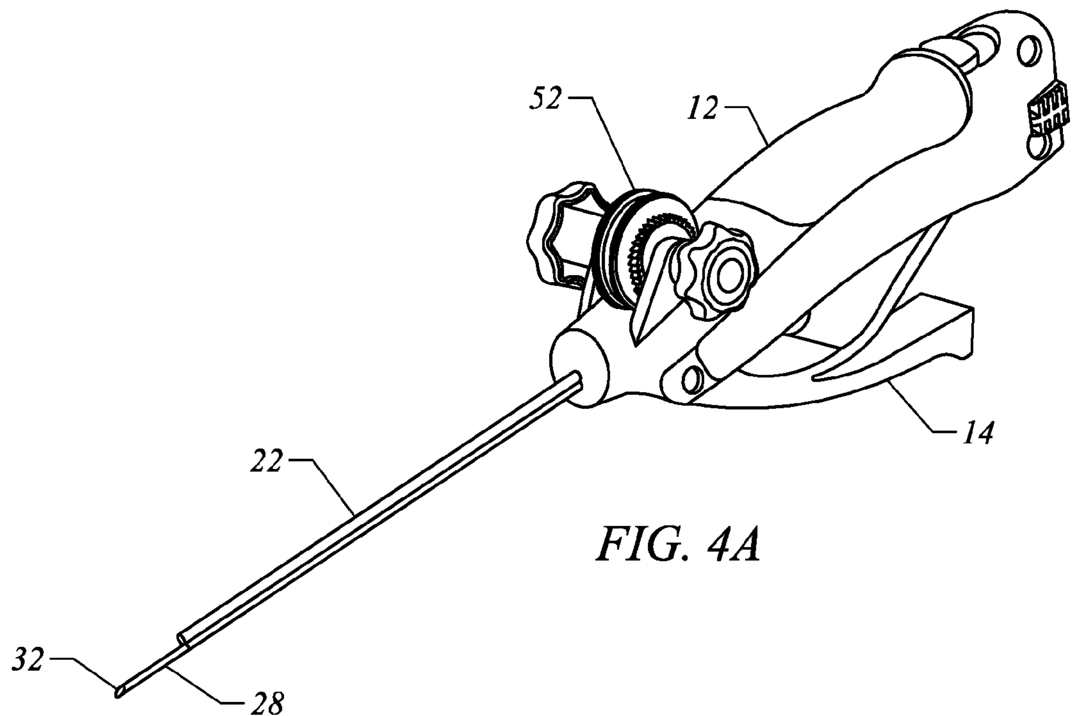
FIGS. 4A and 4B show perspective views of the primary anchor extended and the secondary anchor extended from the barrel support, respectively.
Figure 4B:
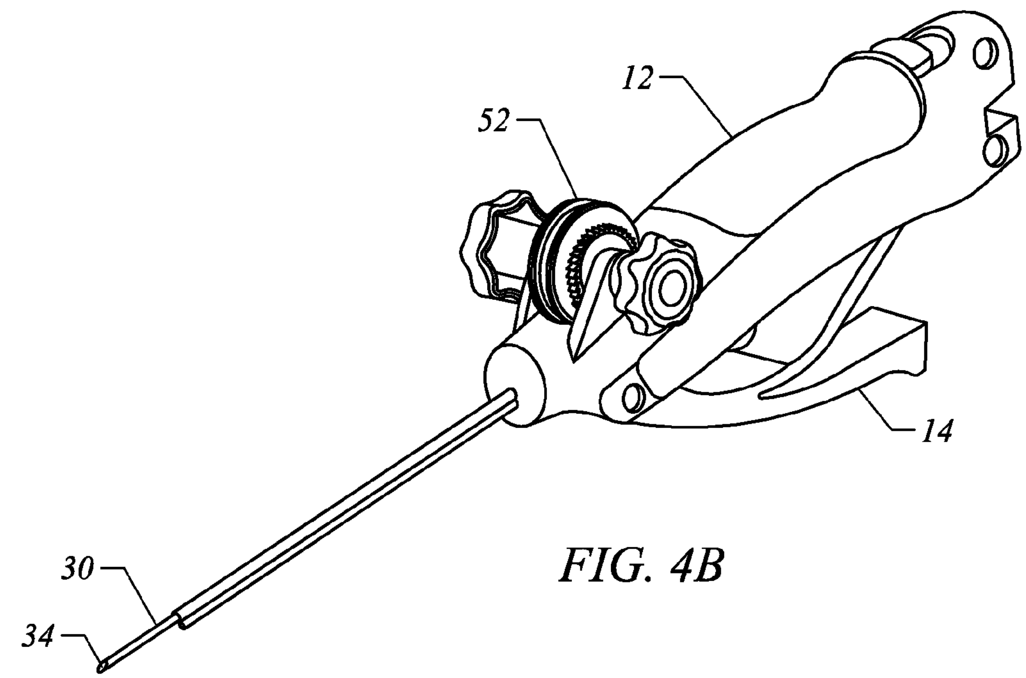

FIG. 3 illustrates a detailed perspective view of handle 12 showing an example of positioning of function switch 48 with respect to primary and secondary driver blocks 44, 46. Also shown are the primary and secondary sleeve lock tabs 36, 38 as well as suture reel 52, which may be actuated by one or both suture reel control knobs 50 and may allow for controlled tightening via a ratchet mechanism as shown or any other suitable cinching or tightening mechanism. As mentioned above, each anchor may be deployed independently of one another and may be actuated from inserter assembly 10 from each respective support sleeve. As shown in the perspective view of FIG. 4A, primary anchor 32 may be deployed from primary support sleeve 28 projected distally of barrel support 22. Once primary anchor 32 has been implanted, primary support sleeve 28 may be partially refracted or withdrawn entirely from handle 12 by removing primary driver block 44, as shown in the perspective view of FIG. 4B, and secondary anchor 34 may be implanted into the underlying bone.

Figure 5A:
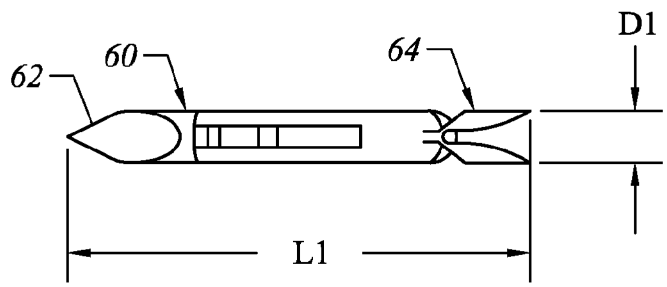
FIGS. 5A and 5B show side views of a variation of an anchor implant having one or more anchor wings in a low-profile delivery configuration and a deployed bone lock configuration, respectively.
Figure 5B:
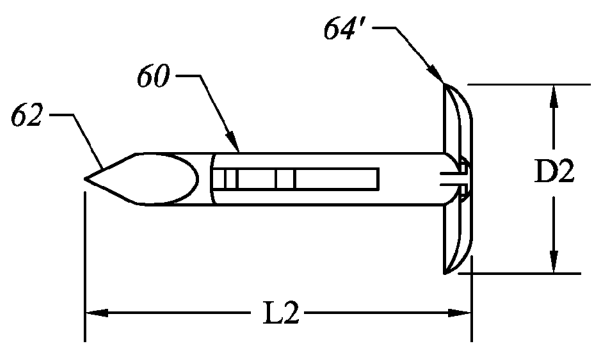

With respect to the anchors, FIGS. 5A and 5B illustrate an example of an anchor in its low-profile delivery configuration and its expanded configuration where the anchor is locked within the bone, respectively. As shown, the anchor may generally comprise an anchor implant body 60 having a piercing tip 62 configured to atraumatically pierce soft tissue and be driven into and through bone. Accordingly, the anchors may be fabricated from a metal such as 316L stainless steel, although other materials such as titanium may be used. In its low-profile configuration, the anchors may have a delivery length L1 (e.g., about 17 mm) and a delivery width D1 (e.g., 1.8 mm) which is suitable for driving into bone. One or more anchor wings 64, which are simply reconfigurable projections extending from a proximal end of anchor body 60, may be angled into a low-profile for delivery into and through the soft tissue and bone, as shown in FIG. 5A.

Once the anchor has been driven through the tissue and implanted into the bone, the anchor wings 64' may be deployed to create a “T” bar which locks the anchor into position within the bone and inhibits or prevents the anchor body 60 from being pulled proximally from the bone, as shown in FIG. 5B. In its deployed configuration, the anchor may have a deployed length L2 (e.g., about 14 mm) and a deployed width D2 (e.g., 6 mm), which may be any width greater than its low-profile diameter depending upon the angle and length at which the deployed anchor wings 64' project from the anchor body 60.

Figure 5C:
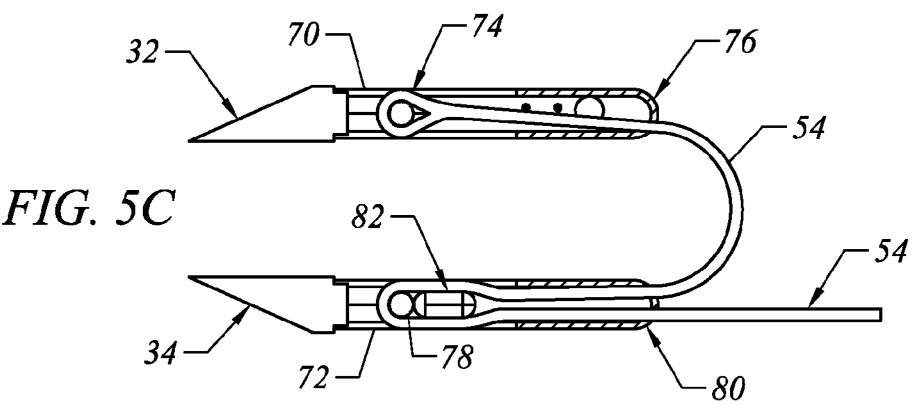
FIGS. 5C and 5D show partial cross-sectional side views of a primary and second anchor interconnected via a length of suture or wire in an adjustable configuration and a cinched and locked configuration, respectively.

FIG. 5C shows a partial cross-sectional side view of an example of primary and secondary anchors 32, 34 inter-connected via the suture or wire 54 and the coupling mechanism connecting the two. Generally, the two anchors 32, 34 may be deployed by the inserter assembly 10 in the same procedure and are connected by the suture or wire 54 which may be varied by the surgeon intra-operatively based upon the placement of the anchors relative to one another. Primary anchor 32 may be preloaded with the suture or wire 54 fixed within the primary anchor body 70 via a primary suture anchor 74 (e.g., a looped end of suture). Suture or wire 54 may extend through a proximal anchor opening 76 and pass into secondary anchor body 72 through a proximal anchor opening 80. There, the suture or wire 54 may be slidingly routed around secondary suture anchor pin 78 and back through anchor opening 80 where suture or wire 54 may extend proximally through the inserter assembly 10 for manipulation and tensioning by the user.

Figure 5D:
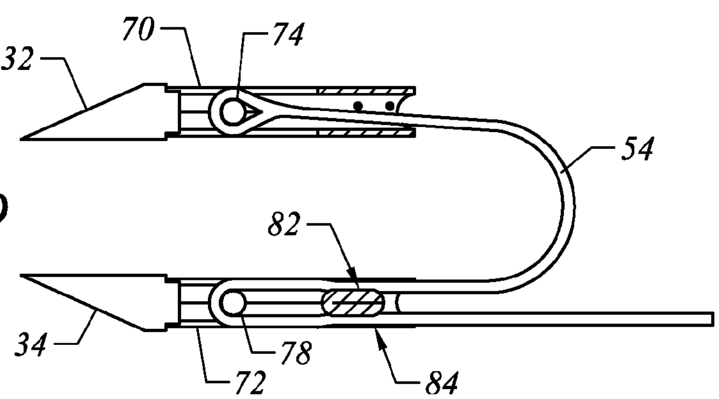

A suture plug 82 may be disposed proximally of secondary suture anchor pin 78 and slidingly retained within secondary anchor body 72 but prohibited from sliding out of anchor opening 80 by tabs extending from the suture plug 82 and riding in slots disposed on both sides of anchor body 72. Once the anchors 32, 34 have been desirably positioned within the bone and the suture or wire 54 tensioned appropriately, suture plug 82 may be urged proximally within secondary anchor body 72 such that the suture or wire 54 passing adjacent to suture plug 82 within anchor body 72 is wedged or compressed along compression zone 84 such that any additional movement of suture or wire 54 relative to the anchors 32, 34 is inhibited and thus locked into position, as shown in FIG. 5D.

Figure 6:
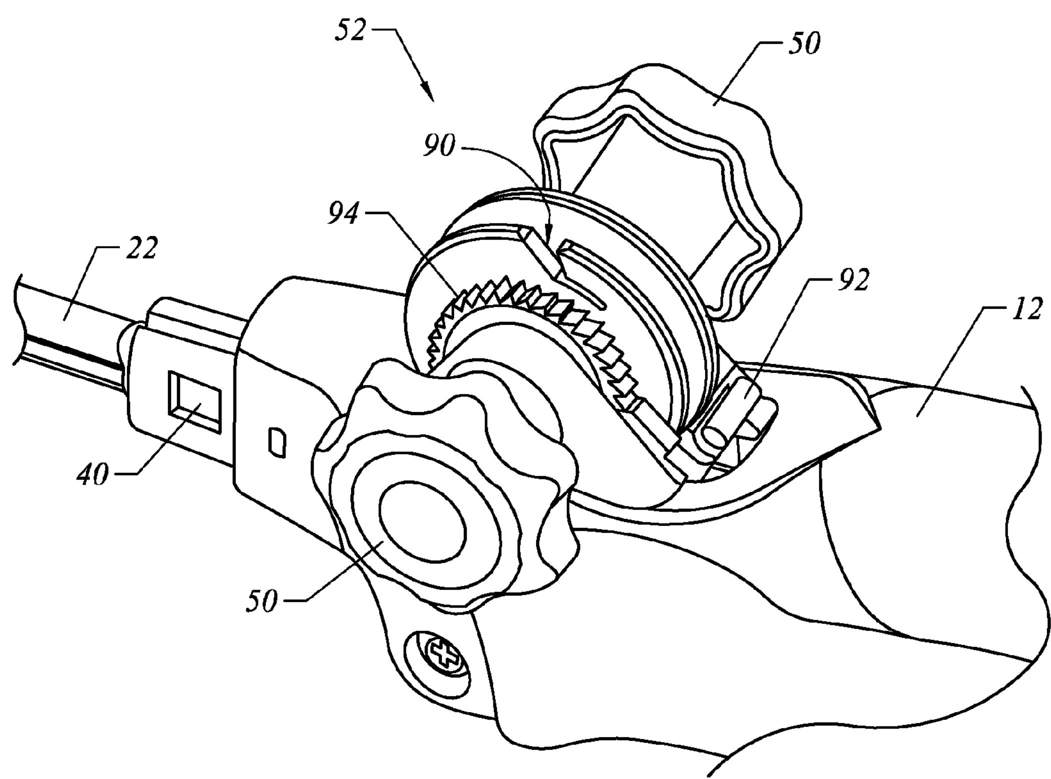
FIG. 6 shows a detailed perspective view of a variation of a suture reel assembly.

To tension the suture or wire 54 in order to approximate the damaged soft tissue against the bone, the suture or wire 54 may be passed through the inserter assembly 10 and through handle 12 for attachment to suture reel 52 located along handle 12, as shown in the detail perspective view of FIG. 6. Suture or wire 54 may be attached along a suture attachment 90 such that when suture reel control knobs 50 are turned in a first direction, the suture or wire 54 may be wound around reel 52 to tighten or tension the suture or wire 54. Reel 52 may include a ratchet mechanism 94 to prevent the accidental release of suture or wire 54 or to inhibit the loosening of the suture or wire 54 by inadvertent rotation of reel 52 in a second opposite direction. Reel 52 may also include ratchet release 92 which may be depressed to release ratchet 94 and allow for the free rotation of reel 52 in either direction to allow for the loosening or adjustment of suture or wire 54 along the tissue.

Figure 7:
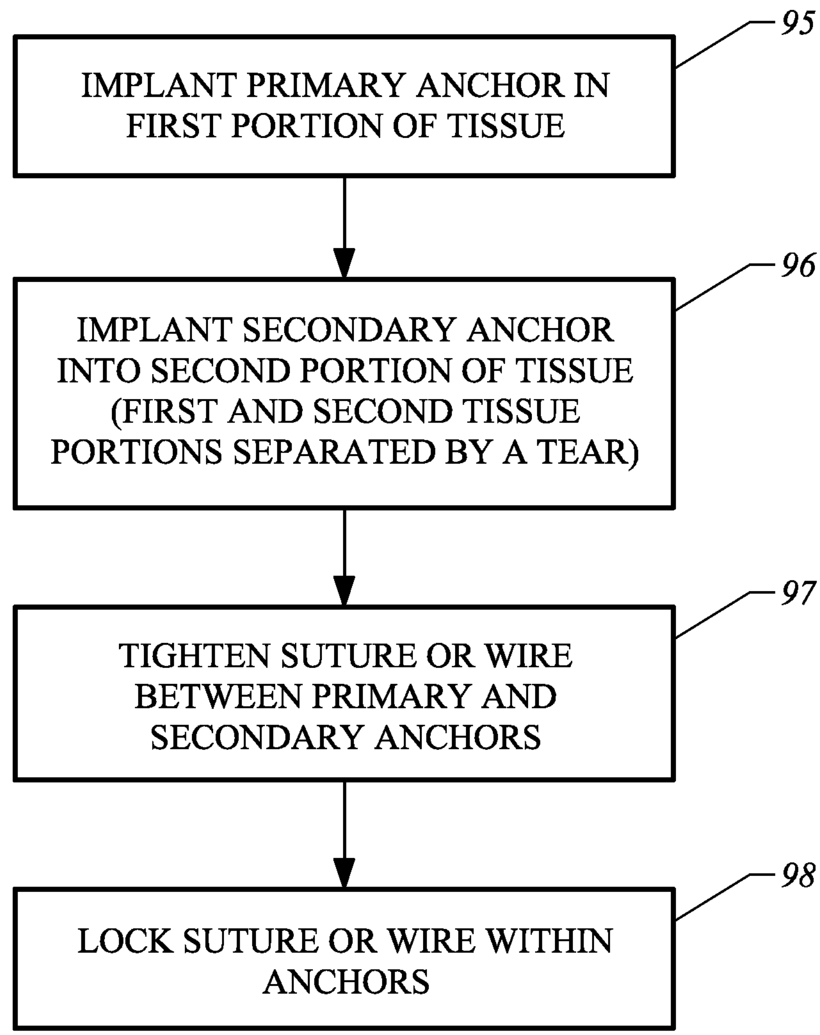
FIG. 7 shows a flow chart illustrating a method for repairing a portion of soft tissue.

In use, as generally illustrated in the flow chart of FIG. 7, the primary anchor 32 may be implanted in a first portion of tissue 95 by piercing the anchor body through the tissue to be repaired and directly into the bone either by pounding the anchor or via pre-drilling an opening into the bone and introducing the anchor into the drilled opening. The primary 32 and/or secondary anchors 34 may be implanted into the bone arthroscopically or optionally via an open procedure. In either case, the assembly may be utilized for applications in treating any tissue tears and for implantation into any bone, as suitable or practicable. Particularly, the devices and methods may be configured or suited for treating the articular supraspinatus tendon with anchor implantation in or around the humeral head.

Once the primary anchor 32 has been implanted into the first portion of tissue, the secondary anchor 34 may be implanted into a second portion of tissue 96 where the first and second tissue portions are separated by a tear to be repaired. With the secondary anchor 34 implanted, the suture or wire may be tightened between the primary and secondary anchors 97 such that the tissue to be repaired is approximated to one another and against the underlying bone. Once suitably tightened, the suture or wire may be locked within the anchors 98 to maintain the tissue approximation.

Figure 8A:
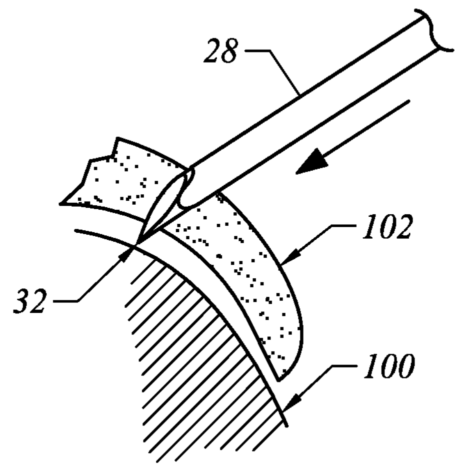
FIG. 8A illustrates a primary anchor being pierced through a soft tissue region to be anchored to a region of underlying bone.
Figure 8B:
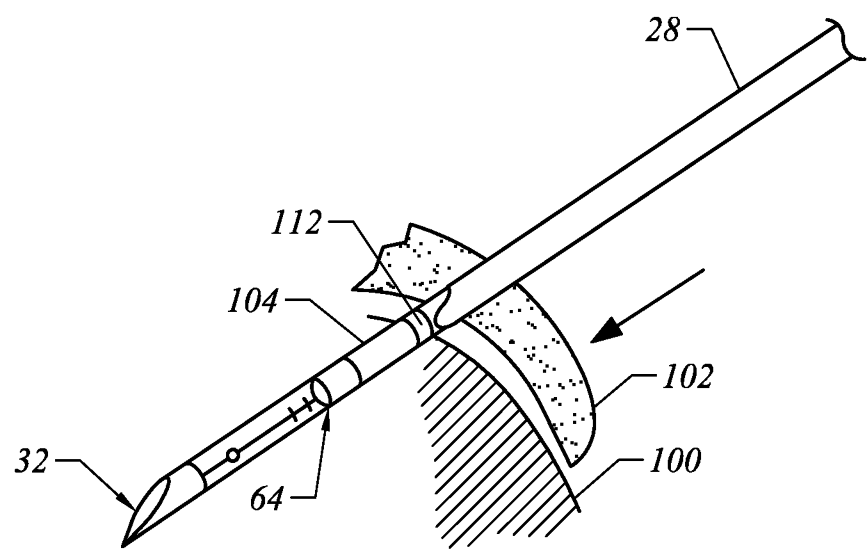
FIG. 8B illustrates the primary anchor being further pierced into the bone while in a low-profile configuration.

Now turning to FIG. 8A, a detailed example is provided for illustrating anchor implantation and suture or wire tightening to repair a soft tissue region. As shown, primary anchor 32 may be inserted through a first portion of the soft tissue 102 to be repaired and brought into contact against the underlying bone region 100. With the piercing tip of primary anchor 32 contacting the bone 100, the primary sleeve lock tab 38 may be removed to release primary support sleeve 28 to slide proximally relative to primary anchor 32 to a distance of, e.g., about 8 mm from a proximal end of anchor 32. A proximal end of the inserter handle 12 may be tapped, e.g., by using a mallet, to drive the primary anchor 32 disposed upon hypotube driver 104 into the bone at a depth of, for example, about 6 mm, as primary support sleeve 28 remains above the bone surface, as shown in FIG. 8B. If viewed through an arthroscope, primary anchor 32 may be driven into the underlying bone 100 until an anchor depth indicator 112, e.g., a colored marking or gradation, located along driver 104 is visible just above or at the bone 100 as a visual indicator the user that the appropriate depth for anchor insertion has been reached. Anchor depth indicator 112 may be located along driver 104 at a distance of, e.g., about 6 mm, from a distal end of driver 104 proximal to the anchor. A depth indicator may also be visible through window 40 along barrel support 22 at the proximal end of the primary support sleeve 28 to indicate to the user when primary anchor 32 has been driven an appropriate depth into the bone.

Figure 8C:
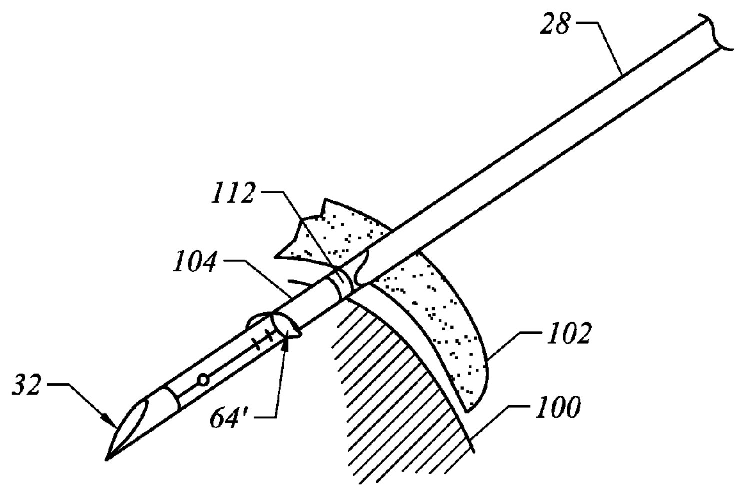
FIG. 8C illustrates the anchor wings along the primary anchor deployed within the bone to lock the anchor within the bone region.
Figure 8D:
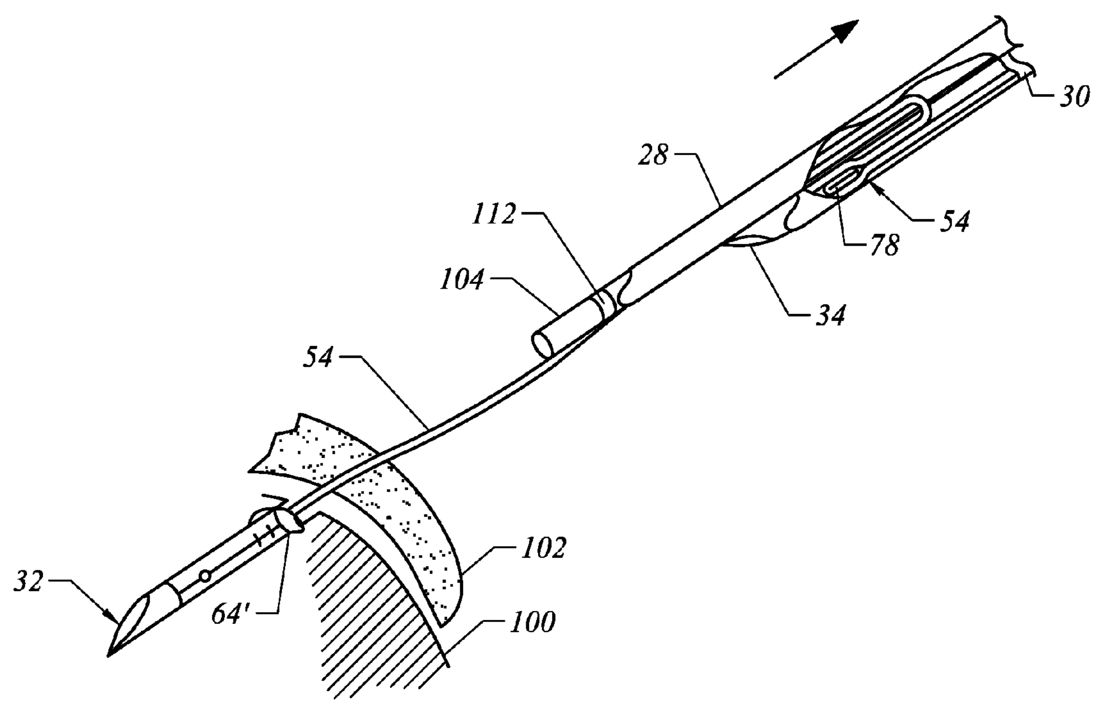
FIG. 8D illustrates the implanted primary anchor released from the inserter assembly and remaining within the bone and having a length of suture or wire extending from the primary anchor.

With primary anchor suitably implanted, the anchor wings 64' may be deployed within the bone 100 by actuating hand lever 14 once to lock a position of anchor 32 and to prevent or inhibit primary anchor 32 from being pulled out of bone 100, as shown in FIG. 8C. Function switch 48 may be depressed and hand lever 14 actuated again to release primary anchor 32 from hypotube driver 104, e.g., by breaking a weld or other suitable coupling temporarily holding primary anchor 32 onto driver 104. Following primary anchor 32 deployment, primary driver block 124 and primary support sleeve 28 may be removed entirely from inserter assembly 10 to allow for placement and implantation of secondary anchor 34 into the tissue, as shown in FIG. 8D. Suture or wire 54 may be seen attached to primary anchor 32 and passing through the soft tissue 102 to be repaired.

Figure 8E:
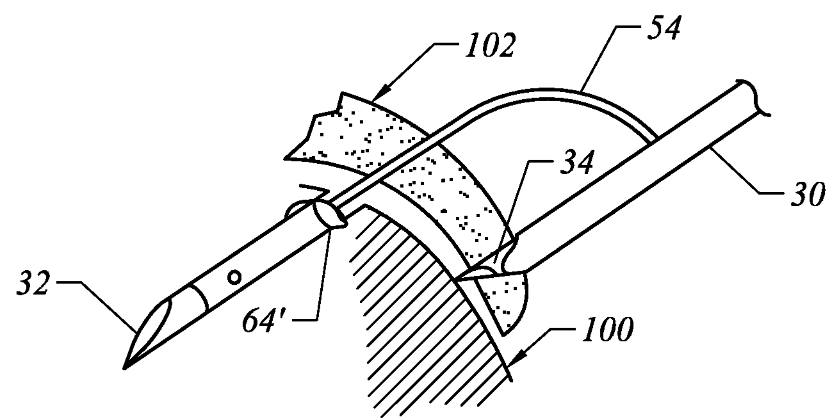
FIG. 8E illustrates the secondary anchor being pierced through the soft tissue region at a location adjacent or proximate to the implanted primary anchor.
Figure 8F:
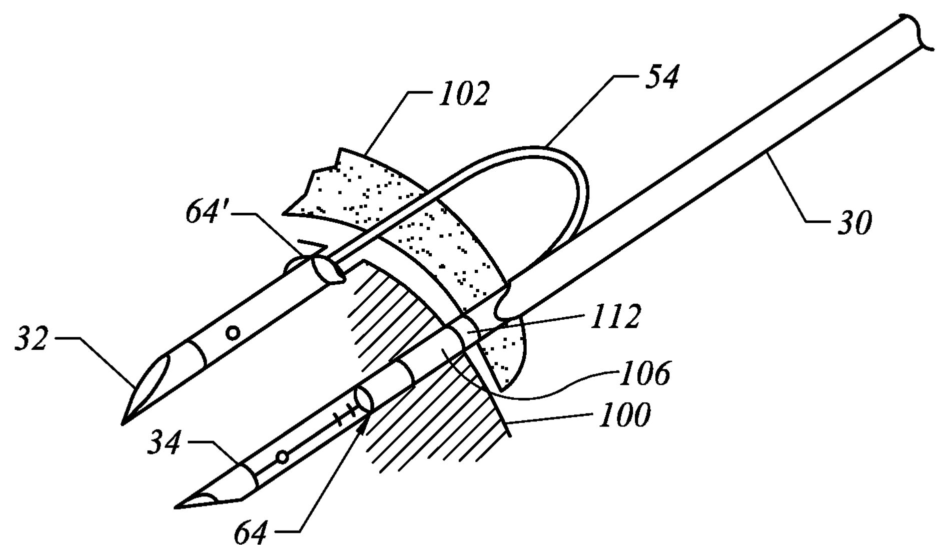
FIG. 8F illustrates the secondary anchor being further pierced into the bone while in a low-profile configuration.

FIG. 8E illustrates the positioning and placement of secondary anchor 34 at a second region of tissue 102 by passing secondary anchor 34 through the tissue 102 and into contact against the underlying bone 100. The anchors 32, 34 are desirably placed at a distance of at least about 5 mm apart, although they may be placed closer to or farther from one another as selected by the surgeon. The maximum distance by which the anchors 32, 34 are positioned apart from one another may be determined by the surgeon as appropriate for the surgical repair. In either case, a damaged or torn region of the tissue 102 to be repaired may preferably be positioned between where the anchors 32, 34 are implanted. Once the secondary anchor 34 has been suitably positioned through the tissue 102 and along the bone 100, the secondary sleeve lock tab 38 may be removed to release the secondary support sleeve 30 to slide proximally relative to secondary anchor 34. Similar to the implantation of primary anchor 32, a proximal end of the inserter handle 12 may be tapped, e.g., by using a mallet, to drive the secondary anchor 34 disposed upon hypotube driver 106 into the bone until anchor depth indicator 112 has been reached as secondary support sleeve 30 remains above the bone surface, as shown in FIG. 8F.

Figure 8G:
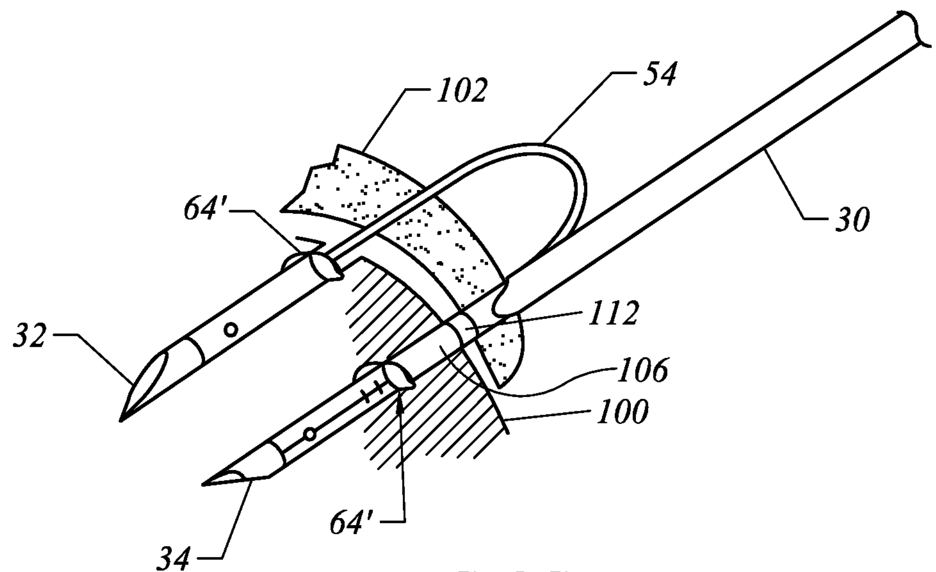
FIG. 8G illustrates the anchor wings along the secondary anchor deployed within the bone.
Figure 8H:
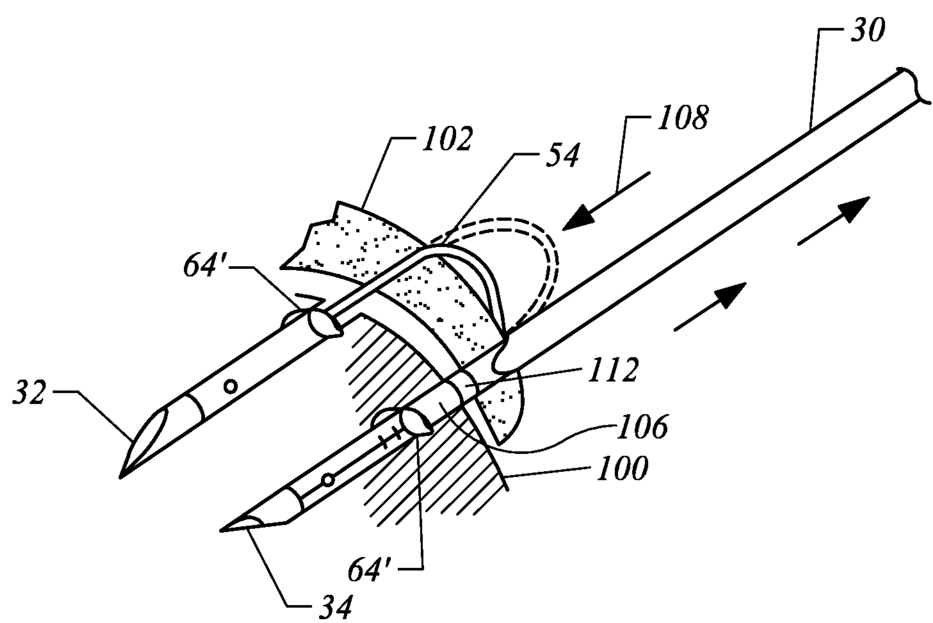
FIG. 8H illustrates the length of suture or wire extending between the primary and secondary anchors being cinched towards one another to hold the region of soft tissue between the two anchors affixed against the bone.

Once secondary anchor 34 has been implanted into bone 100 to a suitable depth, again determined by an indicator visible to the user through window 40, anchor wings 64' may be deployed along secondary anchor 34 to lock the anchor in place within bone 100, as shown in FIG. 8G, by actuating hand lever 14 once on handle 12. With both anchors 32, 34 now implanted through the tissue 102 and within bone 100, the length of suture or wire 54 may be tensioned through the anchors 32, 34 (as indicated by the direction of suture tightening 108 in FIG. 8H) and up into handle 12 by wrapping the suture around suture reel 52, as above.

Figure 8I:
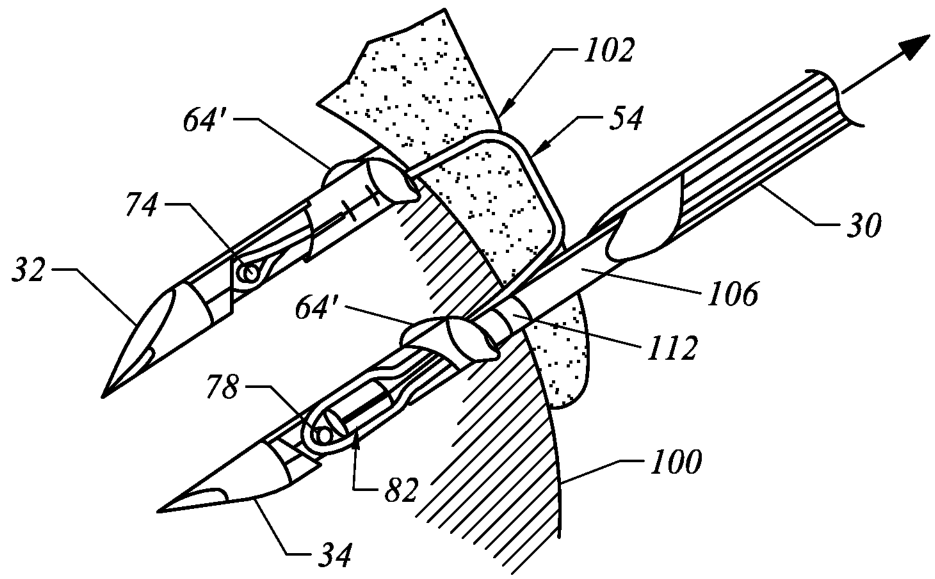
FIGS. 8I and 8J illustrate the length of suture or wire being tensioned while a suture plug is retracted within the secondary anchor to maintain or lock the suture or wire with respect to the implanted anchors.
Figure 8J:
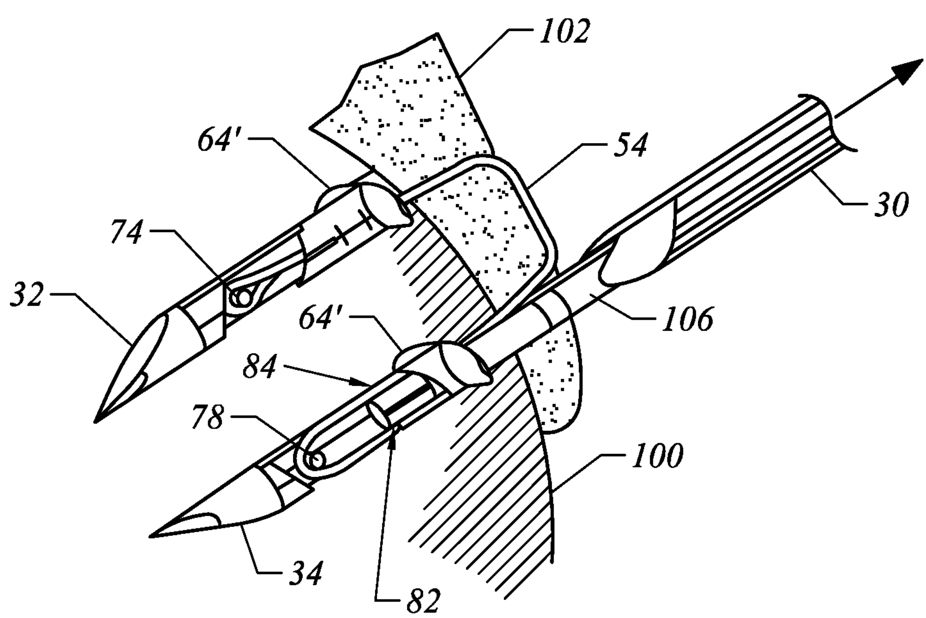
Figure 8K:
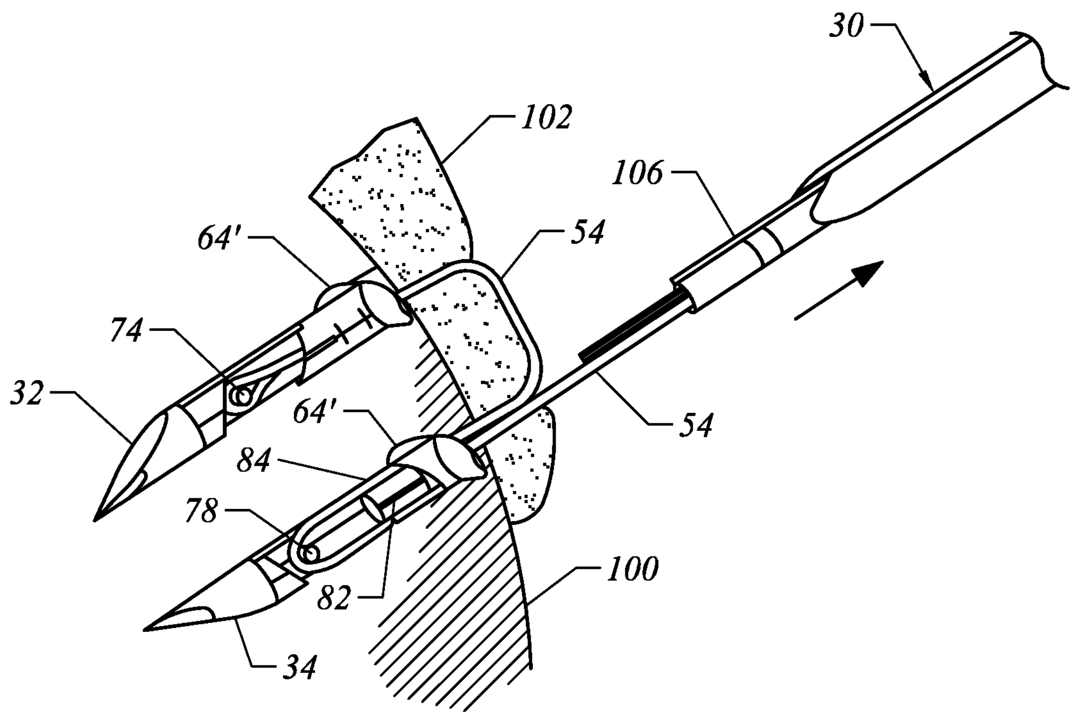
FIG. 8K illustrates the detachment and removal of the inserter assembly from the secondary anchor.
Figure 8L:
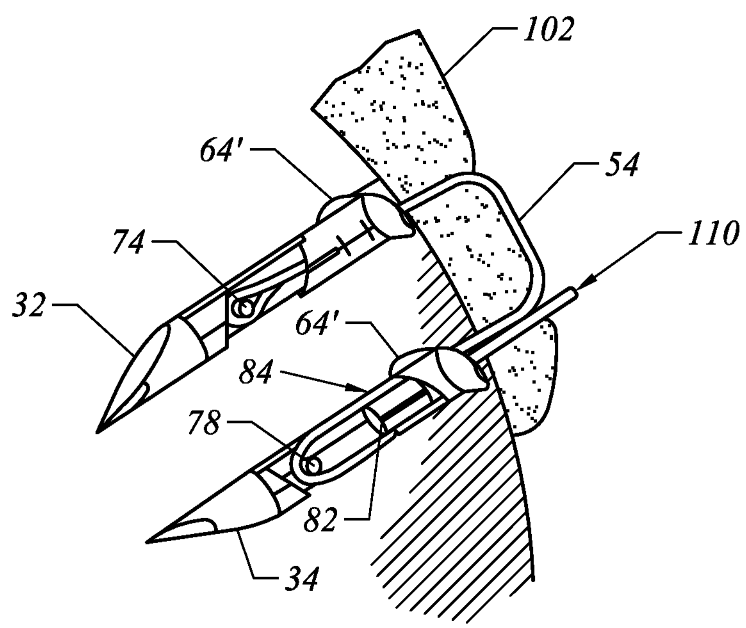
FIG. 8L illustrates the trimmed suture or wire and the implanted anchors retaining the soft tissue to the bone region.

With suture or wire 54 now tensioned and approximating the tissue 102 against one another and against the bone 100, suture plug 82 may be retracted proximally through secondary anchor 34, as shown in FIG. 8I, by depressing hand lever 14 a second time until suture plug 82 is pulled into compression zone 84 where suture or wire 54 is locked relative to the anchors 32, 34, as shown in FIG. 8J. With suture or wire 54 maintained in a tensioned state between the anchors 32, 34, secondary anchor 34 may be released from hypotube driver 106, e.g., by breaking a weld or other suitable coupling temporarily holding secondary anchor 34 onto driver 106, as shown in FIG. 8K. The length of suture or wire 54 proximal to second anchor 34 may be trimmed 110 to complete the procedure and leave the implanted anchors 32, 34 and tensioned suture or wire 54 within the bone and repaired soft tissue 102, as shown in FIG. 8L.

Figure 9:
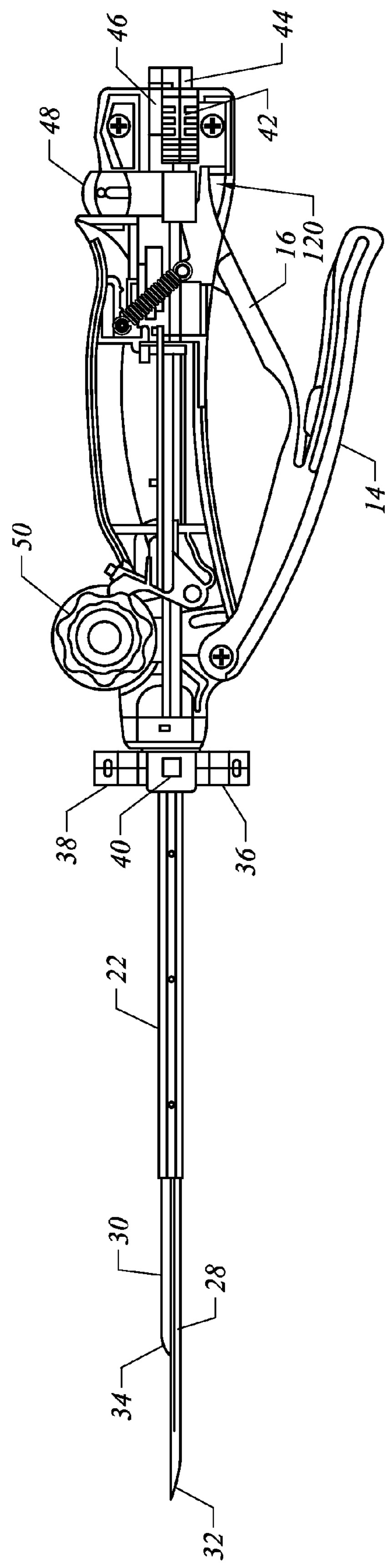
FIG. 9 illustrates a side view of an anchor inserter assembly having the handle partially removed to reveal the mechanisms within.
Figure 10A:
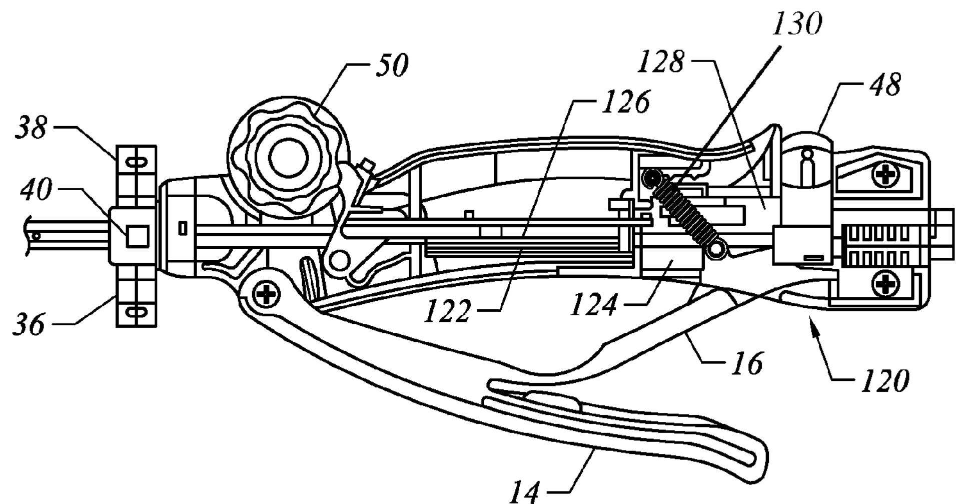
FIGS. 10A and 10B show a side view of the handle interior and partial cross-sectional side view of the handle, respectively, illustrating the primary and secondary driver block mechanisms.
Figure 10B:
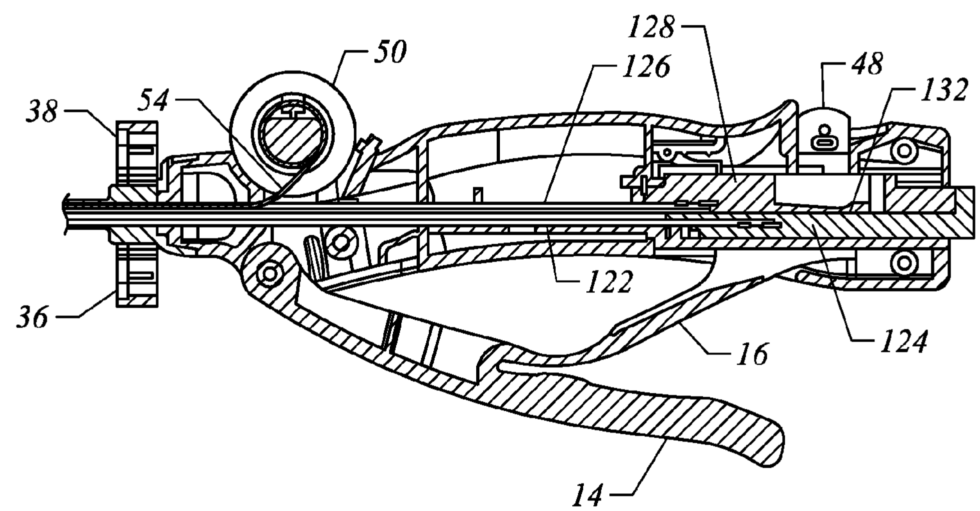

With the anchor inserter assembly 10 and method for anchor insertion described above, details of the handle assembly 12 mechanisms for deploying the respective anchors into the tissue are described below. For instance, FIG. 9 illustrates a side view of the anchor inserter assembly having handle 12 partially removed to reveal the coupling mechanisms 120 within. FIGS. 10A and 10B show a more detailed side view of the handle interior and partial cross-sectional side view of the handle, respectively, illustrating the primary driver 122 (from which primary support sleeve 28 and driver 104 are coupled) to primary driver block 124 and secondary driver 126 (from which secondary support sleeve 30 and driver 106 are coupled) to secondary driver block 128. A biasing element 130, e.g., spring, may be seen coupled between handle 12 and an end of lever 16 which maintains lever 16 and hand lever 14 in contact against either primary driver block 124 or secondary driver block 126 during deployment, as shown in FIG. 10A. Also shown are anti-backlash teeth 132 engaged between primary and secondary driver blocks 124, 126 to prevent the relative movement between the blocks 124, 126 during anchor deployment and movement of the mechanisms 120, as shown in FIG. 10B.

Figure 11A:
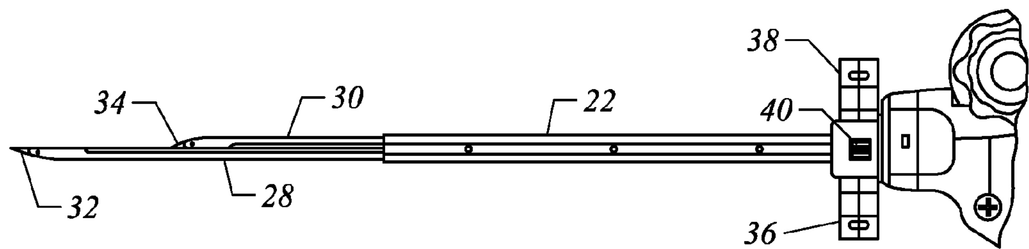
FIGS. 11A to 11C illustrate the removal of a primary sleeve lock tab and the resulting refraction of the primary support sleeve to reveal the primary anchor.
Figure 11B:
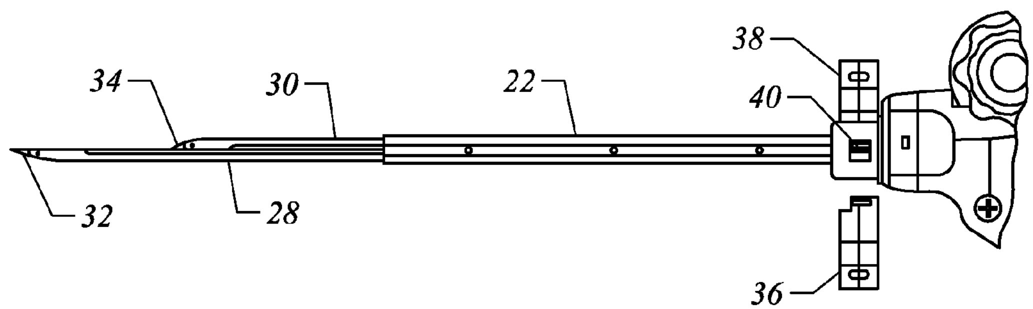
Figure 11C:
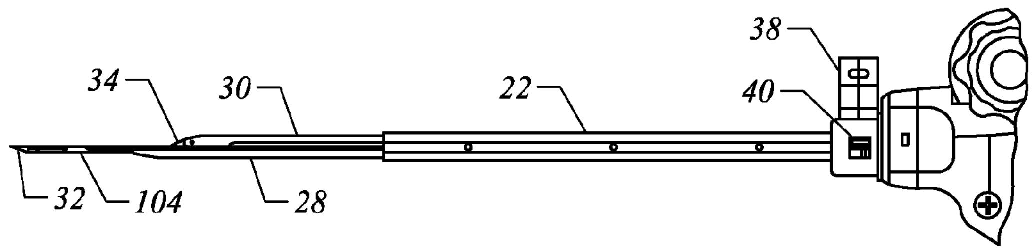
Figure 12:
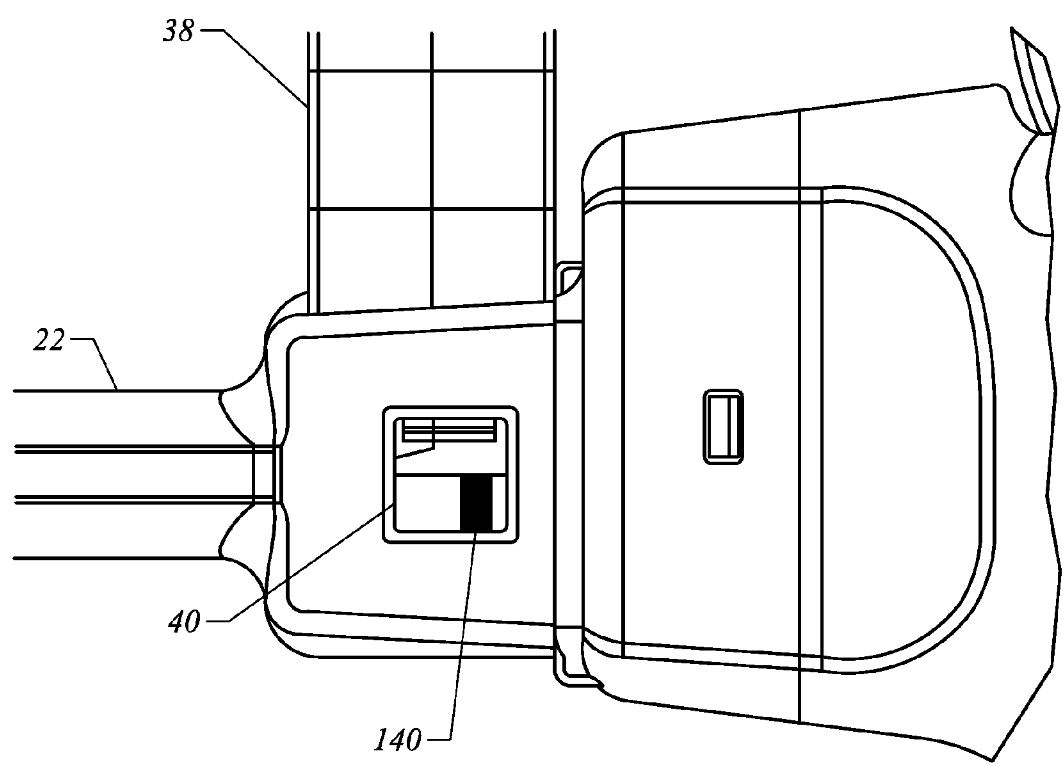
FIG. 12 shows a detailed side view of a primary anchor depth mark within a viewing window indicating that the primary anchor has been driven to an appropriate depth within the bone.

As described above, when primary anchor 32 is to be driven into the bone, primary support sleeve 28 is retracted relative to anchor 32. FIGS. 11A and 11B show the removal of primary sleeve lock tab 36 from inserter assembly 10 to release the primary support sleeve 28 to move such that primary anchor 32 is exposed, as shown in FIG. 11C. Also, once lock tab 36 is removed, window 40 may expose primary anchor depth mark 140 disposed along a proximal portion of primary support sleeve 28. As primary anchor 32 is driven into the bone, sleeve 28 is moved proximally relative to anchor 32 and anchor 32 may be advanced into the bone until primary anchor depth mark 140 becomes visible within window 40. When visible, this is an indication that the anchor 32 has been driven into the bone to a suitable depth, as illustrated in FIG. 12.

Figure 13A:
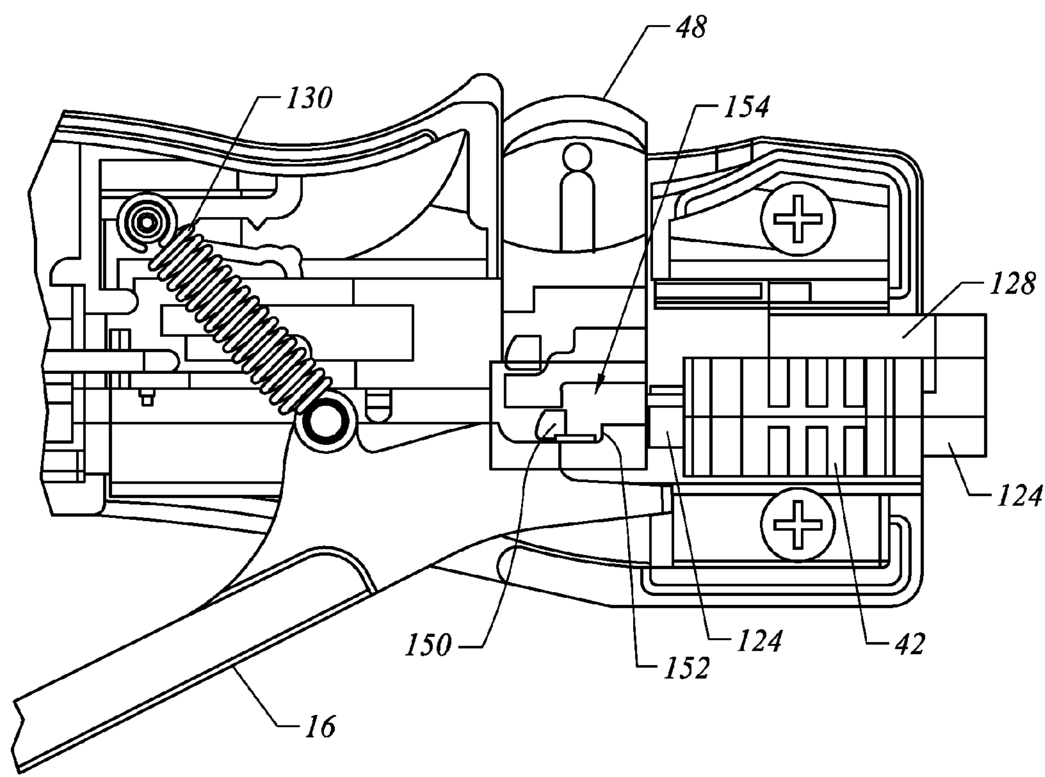
FIGS. 13A and 13B illustrate a side view of the retraction of the primary driver block within the handle and a perspective view of the resulting retracted sleeve, respectively.
Figure 13B:
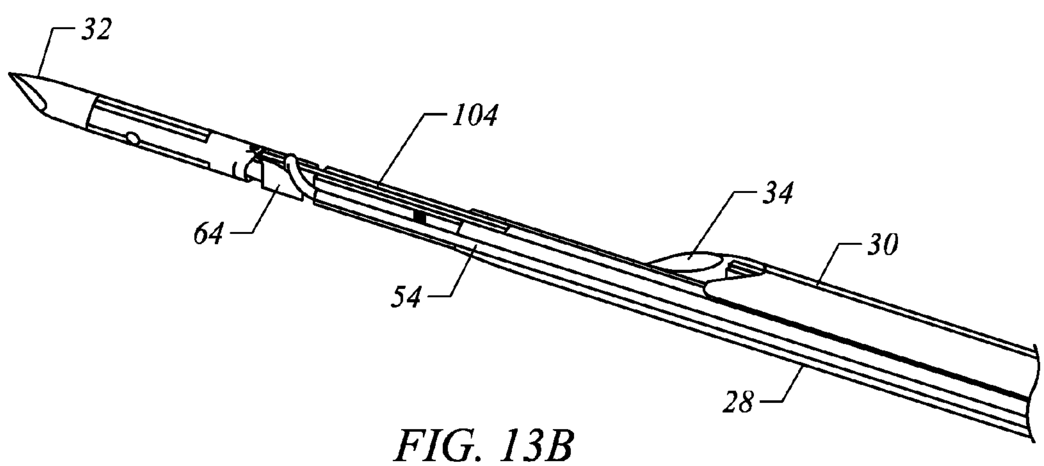

FIGS. 13A and 13B further illustrate a side view of the retraction of primary driver block 124 within the handle 12 and a perspective view of the resulting retracted sleeve 28 and exposed anchor 32, respectively. As shown, primary driver block 124 may define a primary block engagement tab 150 which is free to slide within primary block guide channel 154 defined along the function switch 48, as shown in FIG. 13A. As hand lever 14 is depressed, lever 16 within handle 12 is forced proximally into engagement with primary block engagement tab 150, which in turn urges primary driver block 124 proximally until tab 150 is stopped by contacting function switch stop 152. The retraction of primary support sleeve 28 is accordingly halted leaving primary anchor 32 exposed, as described above and as shown in FIG. 13B.

Figure 14A:
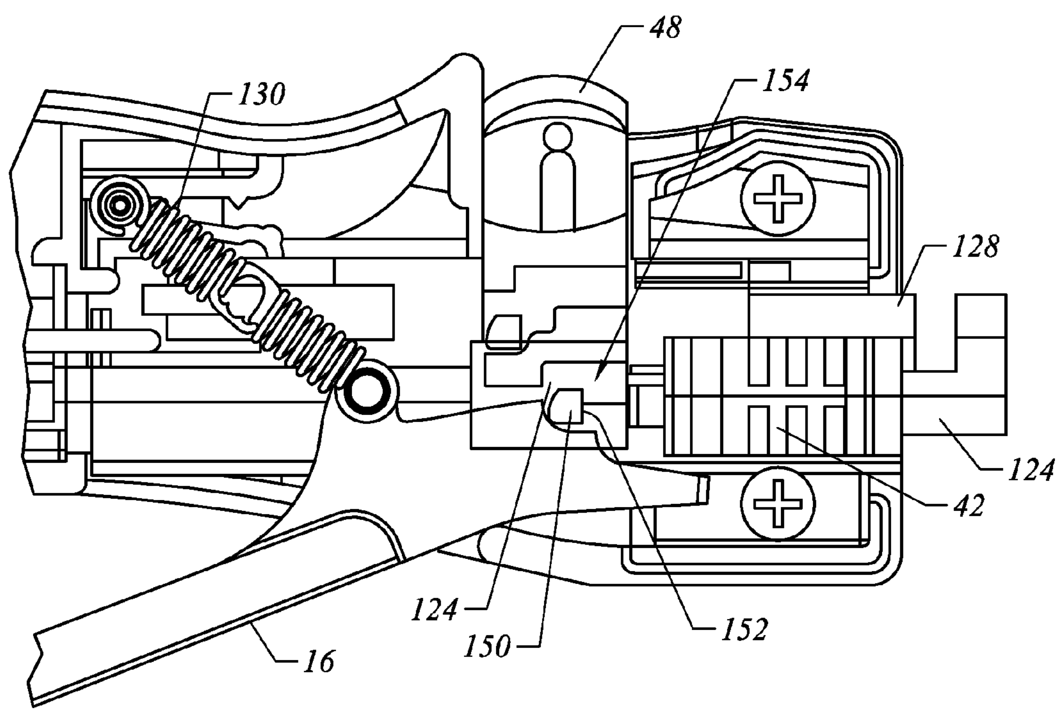
FIGS. 14A and 14B illustrate a side view of the partial retraction of the primary driver block within the handle and a perspective view of the partially deployed wings, respectively.
Figure 14B:
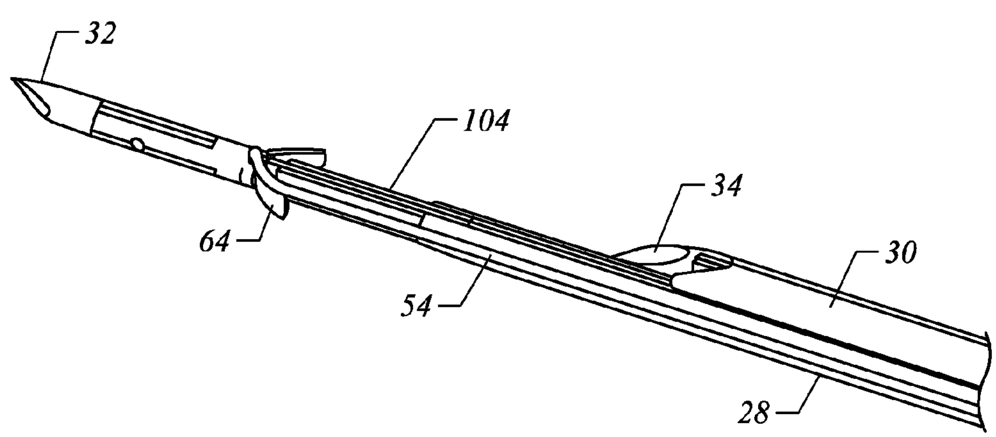

With primary anchor 32 desirably positioned within the bone, as above, anchor wings 64 may be deployed to lock the anchor in place. Accordingly, function switch 48 may be depressed by the user such that switch 48 is moved transversely relative to engagement tab 150 to release the tab 150 from function switch stop 152, as shown in the exposed side view of FIG. 14A. Primary driver block 124 may then be further urged by lever 16 to retract along primary block guide channel 154 to begin the deployment of anchor wings 64, as shown in the perspective view of FIG. 14B.

Figure 15A:
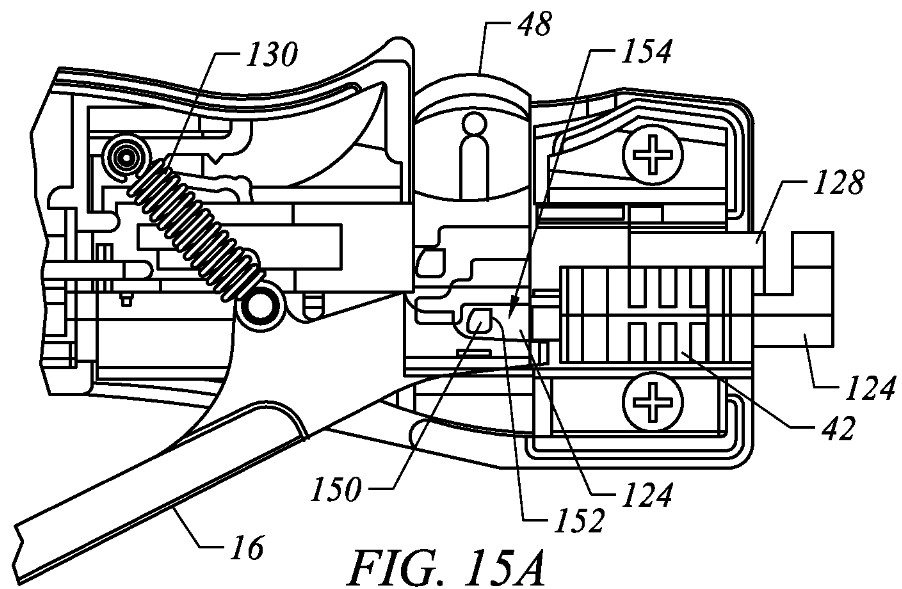
FIGS. 15A to 15C illustrate the further retraction of the primary driver block within the handle and a perspective view of the fully deployed anchor wings, respectively.
Figure 15B:
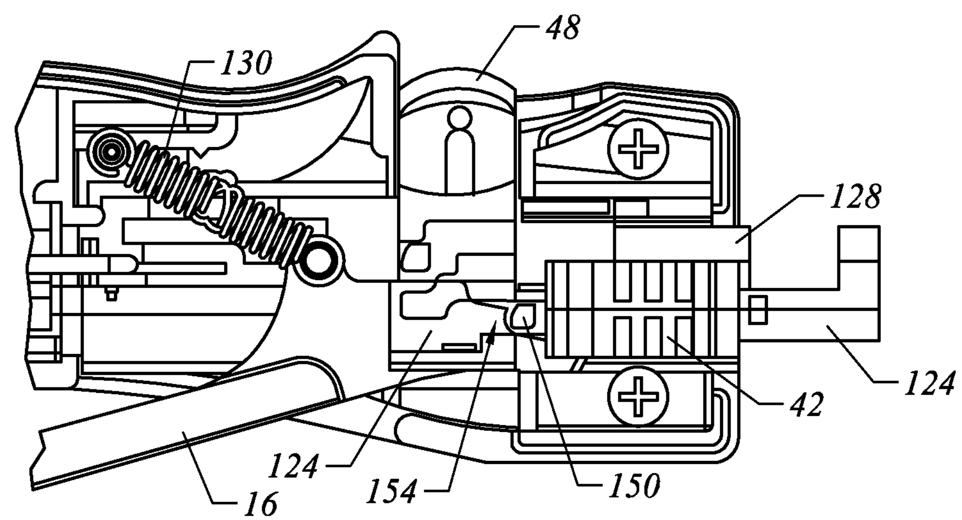
Figure 15C:
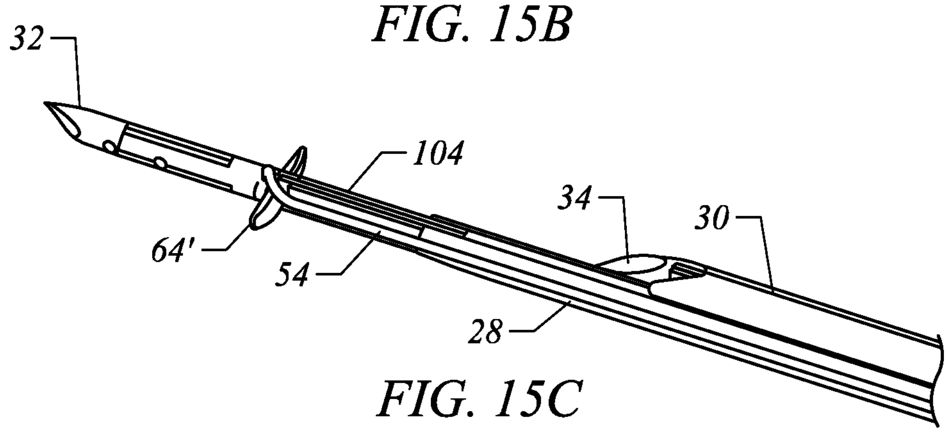
Figure 16A:
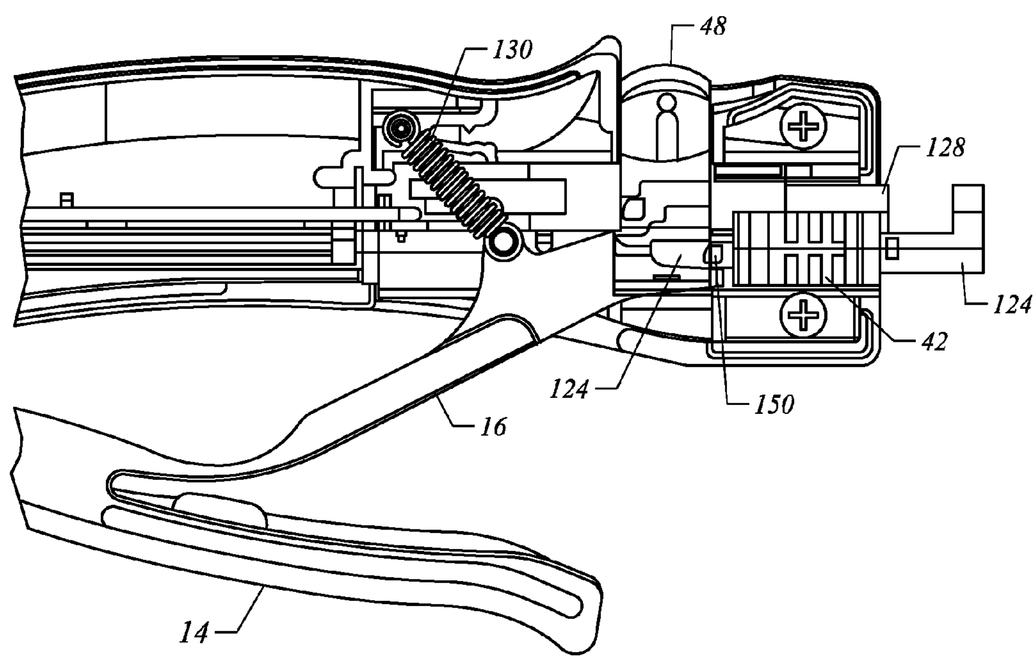
FIGS. 16A and 16B illustrate a side view of a partially exposed handle showing the retracted primary driver block and removal of the primary driver block assembly from the inserter assembly.
Figure 16B:
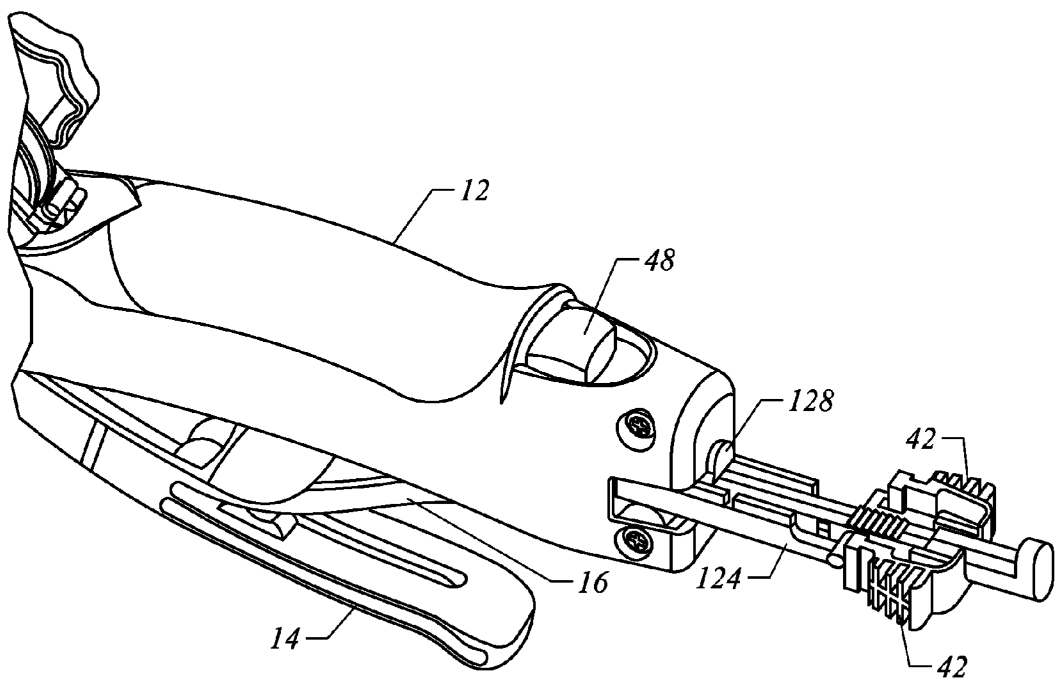

To fully deploy anchor wings 64' within the bone to lock primary anchor 32 in place and to break the weld between the primary anchor 32 and the driver 104, primary driver block 124 may be further urged proximally by the engagement of lever 16 to engagement tab 150 such that primary driver block 124 is fully retracted within the handle, as shown in FIGS. 15A and 15B. FIG. 15C illustrates a perspective view of primary anchor 32 having its anchor wings 64' fully deployed. Once primary anchor 32 has been implanted and released from the handle, hand lever 14 and lever 16 may be disengaged from engagement tab 150 by releasing the lever 14, as shown in FIG. 16A and primary support sleeve 28 may be removed entirely from inserter assembly 10 by disengaging primary anchor removal tabs 42 from a proximal portion of handle 12 to allow for primary driver block 124 to be fully removed, as shown in the perspective view of FIG. 16B.

Figure 17A:
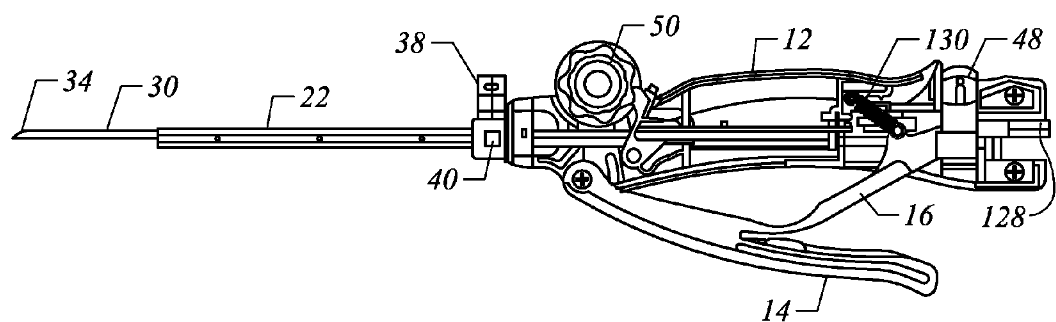
FIGS. 17A and 17B show side views of the exposed handle assembly illustrating engagement of the handle lever with the secondary driver block assembly.
Figure 17B:
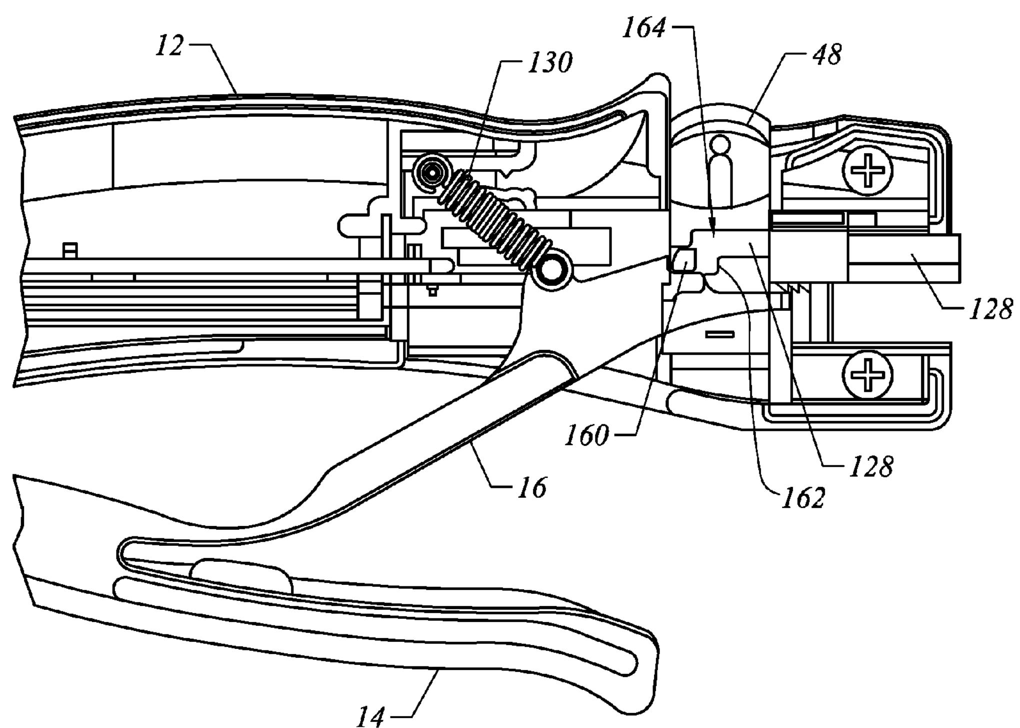

With primary anchor 32 implanted and primary driver block 124 removed from handle 12, secondary anchor 34 and secondary support sleeve 30 remains within inserter assembly 10 for deployment, as shown in FIG. 17A. Thus, secondary anchor 34 may be positioned independently of the implanted primary anchor 32 for placement upon the second region of tissue, as described above. Lever 16 may also be pulled by spring 130 into engagement with secondary block engagement tab 160, which is connected to secondary driver block 128, as shown in the exposed side view of handle 12 in FIG. 17B.

Figure 18A:
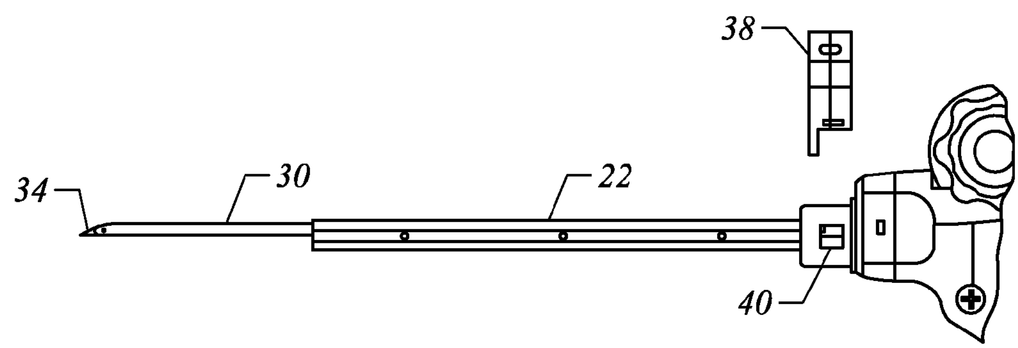
FIGS. 18A and 18B illustrate the removal of a secondary sleeve lock tab and the resulting retraction of the secondary support sleeve to reveal the secondary anchor.
Figure 18B:
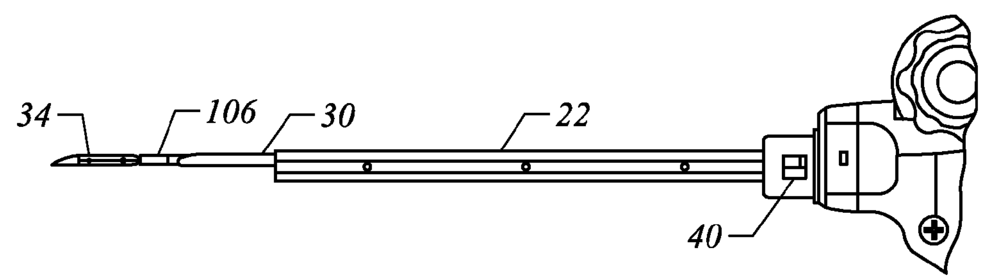
Figure 19:
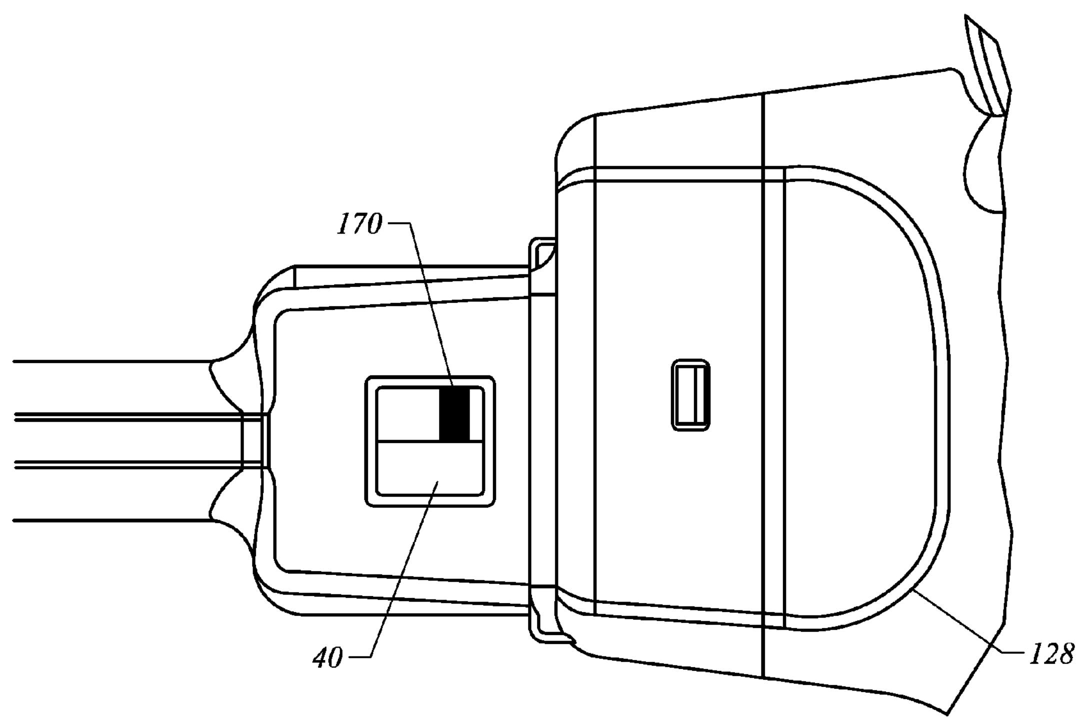
FIG. 19 shows a detailed side view of a secondary anchor depth mark within the viewing window indicating that the secondary anchor has been driven to an appropriate depth within the bone.

To release secondary support sleeve 30, secondary sleeve lock tab 38 may be removed from inserter assembly 10, as shown in FIG. 18A, such that sleeve 30 may be released to retract proximally relative to secondary anchor 34 and driver 106 during anchor implantation, as shown in the side view of FIG. 18B. As above, once lock tab 38 is removed, window 40 may expose secondary anchor depth mark 170 disposed along a proximal portion of secondary support sleeve 30. As secondary anchor 34 is driven into the bone, sleeve 30 is moved proximally relative to anchor 34 and anchor 34 may be advanced into the bone until secondary anchor depth mark 170 becomes visible within window 40. When visible, this is an indication that the anchor 34 has been driven into the bone to a suitable depth, as shown in FIG. 19.

Figure 20A:
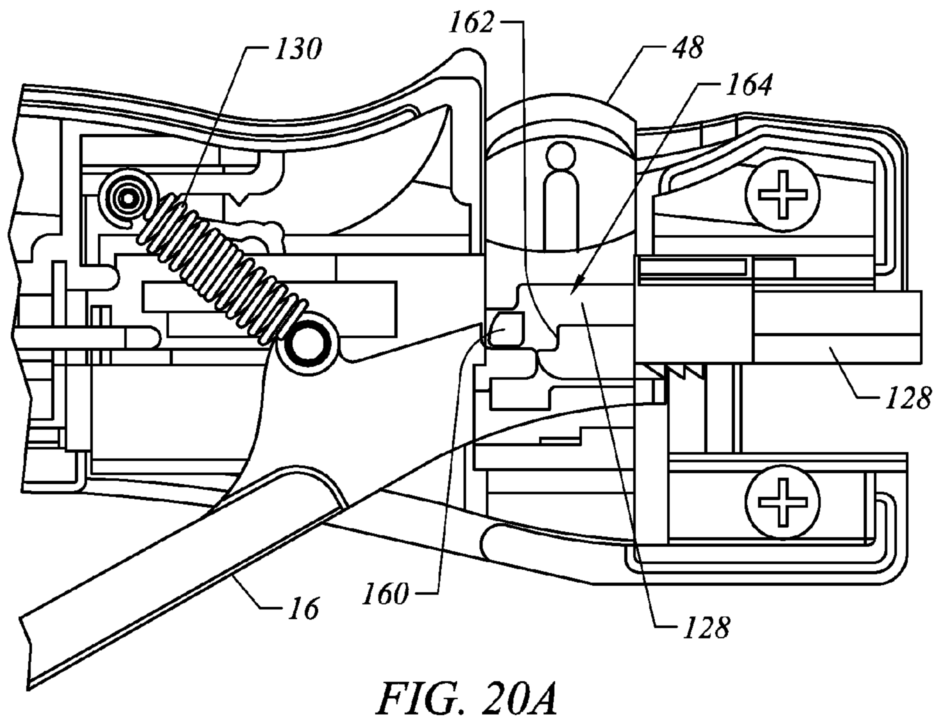
FIGS. 20A and 20B illustrate a side view of the retraction of the secondary driver block within the handle and a perspective view of the resulting retracted sleeve, respectively.
Figure 20B:
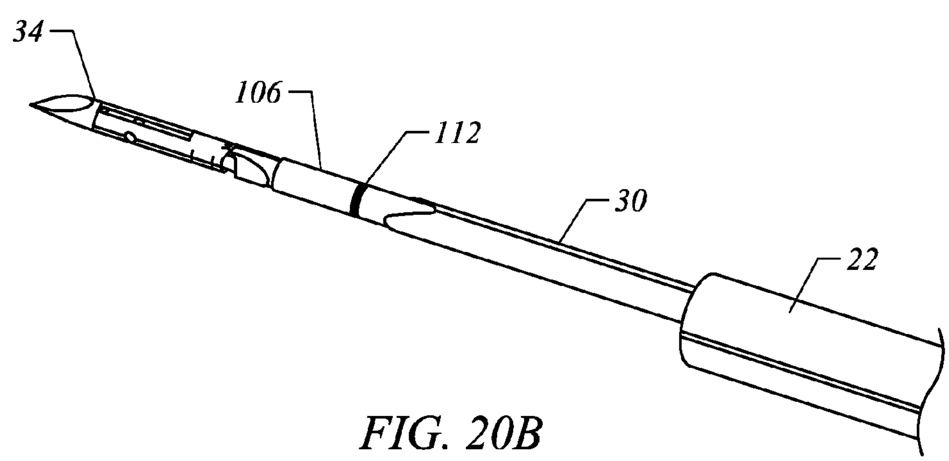

FIG. 20A illustrates a side view of the exposed handle 12 showing the engagement of lever 16 with secondary block engagement tab 160, which is connected to secondary driver block 128 and the retraction of the secondary driver block 128 within the handle 12. FIG. 20B shows a perspective view of the resulting retracted support sleeve 30 for secondary anchor 34 implantation within the bone, as described above.

Figure 21A:
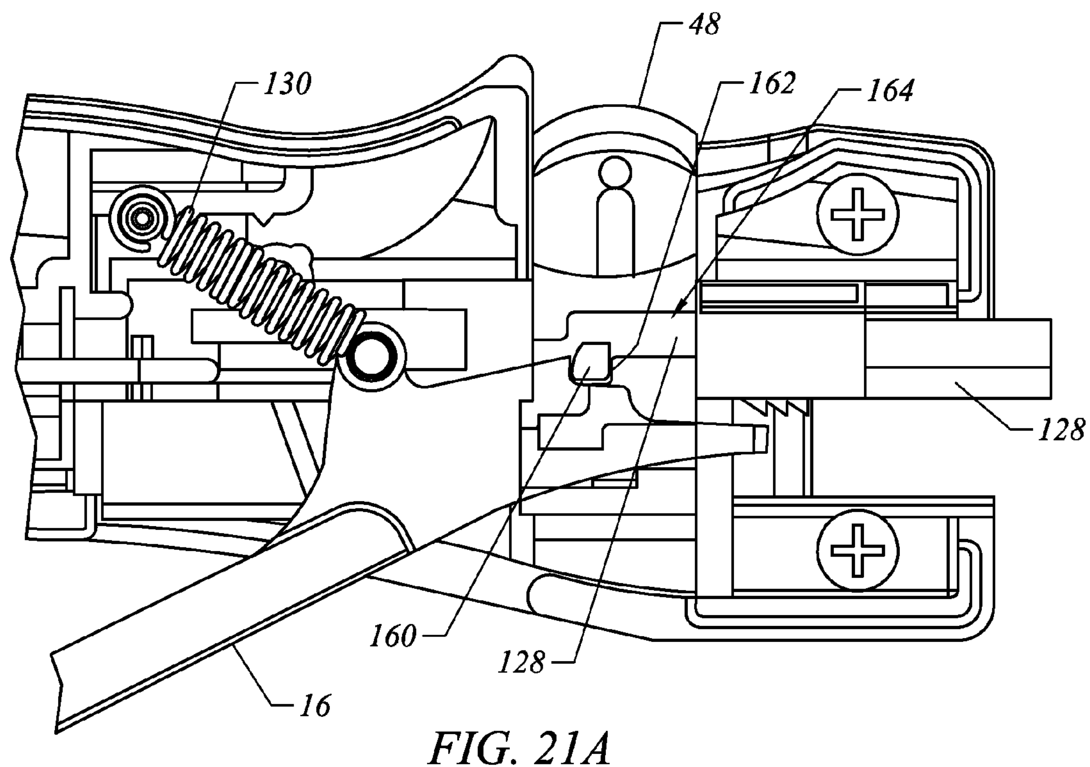
FIGS. 21A and 21B illustrate a side view of the partial retraction of the secondary driver block within the handle and a perspective view of the partially deployed wings, respectively.
Figure 21B:
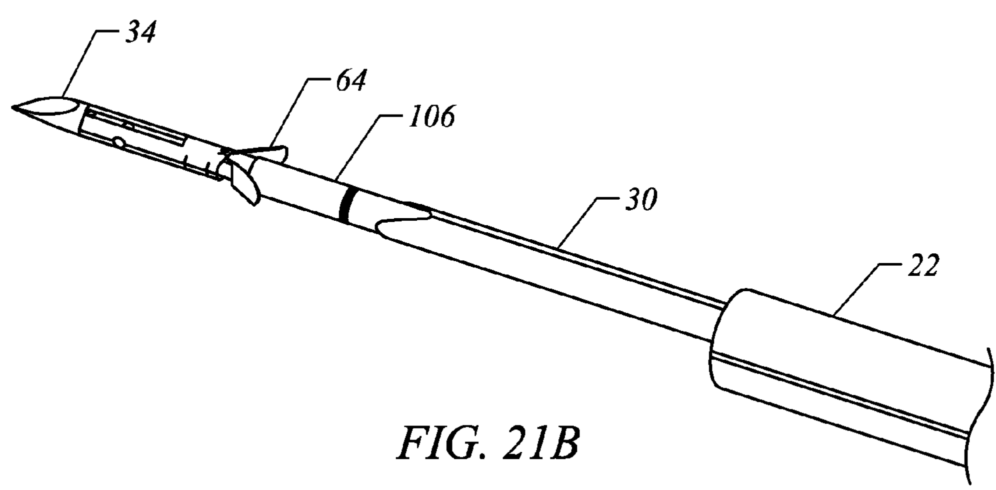
Figure 22A:
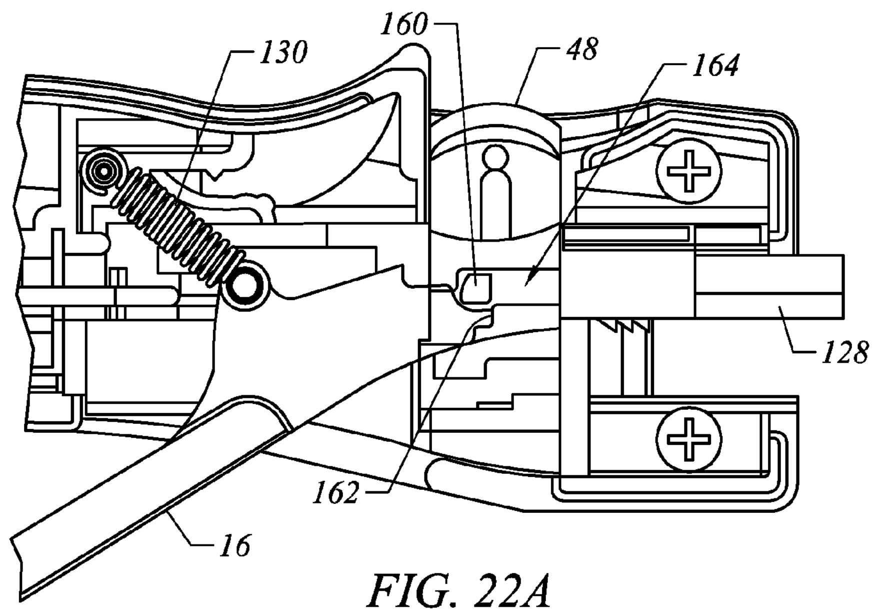
FIGS. 22A to 22C illustrate the further retraction of the secondary driver block within the handle and a perspective view of the fully deployed anchor wings, respectively.
Figure 22B:
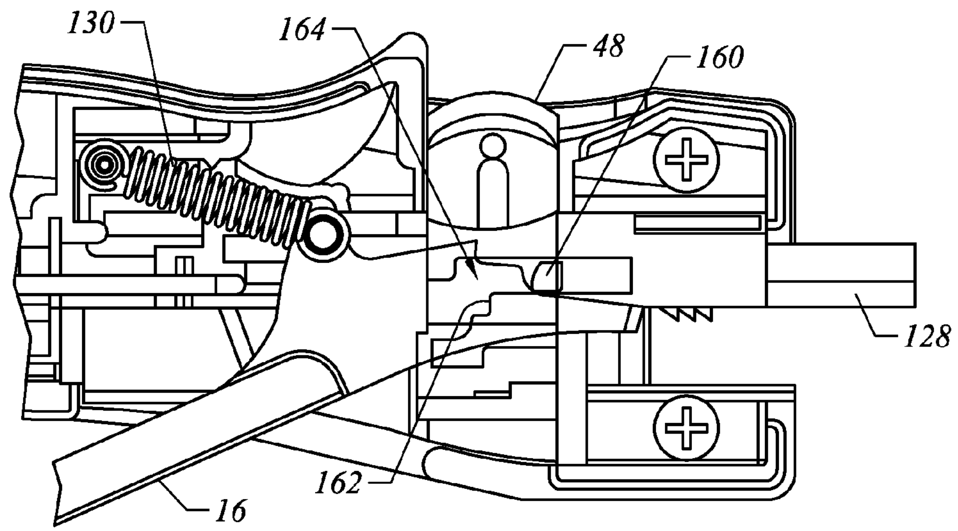
Figure 22C:
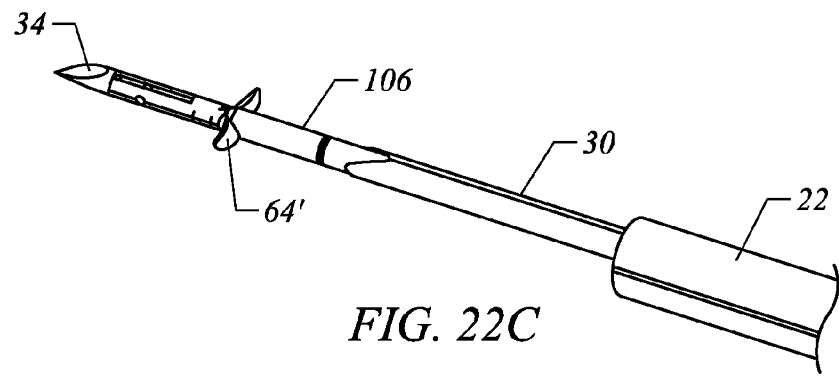

With secondary anchor 34 desirably positioned within the bone near or adjacent to primary anchor 32, anchor wings 64 may be deployed to lock the secondary anchor 34 in place. Accordingly, function switch 48 may be depressed by the user such that switch 48 is again moved transversely relative to secondary block engagement tab 160 to release the tab 160 from function switch stop 162, as shown in the exposed side view of FIG. 21A. Secondary driver block 128 may then be further urged by lever 16 to retract along secondary block guide channel 164 to begin the deployment of anchor wings 64 along secondary anchor 34, as shown in the perspective view of FIG. 21B. It is at this point that the suture or wire 54 is tensioned to approximate the soft tissues to be repaired To fully deploy anchor wings 64' within the bone and to immobilize the tensioned suture or wire 54, and to lock secondary anchor 34 in place, secondary driver block 128 may be further urged proximally by the engagement of lever 16 to engagement tab 160 such that secondary driver block 128 is fully retracted within the handle, as shown in FIGS. 22A and 22B. FIG. 22C illustrates secondary anchor 34 having its anchor wings 64' fully deployed.

Figure 23A:
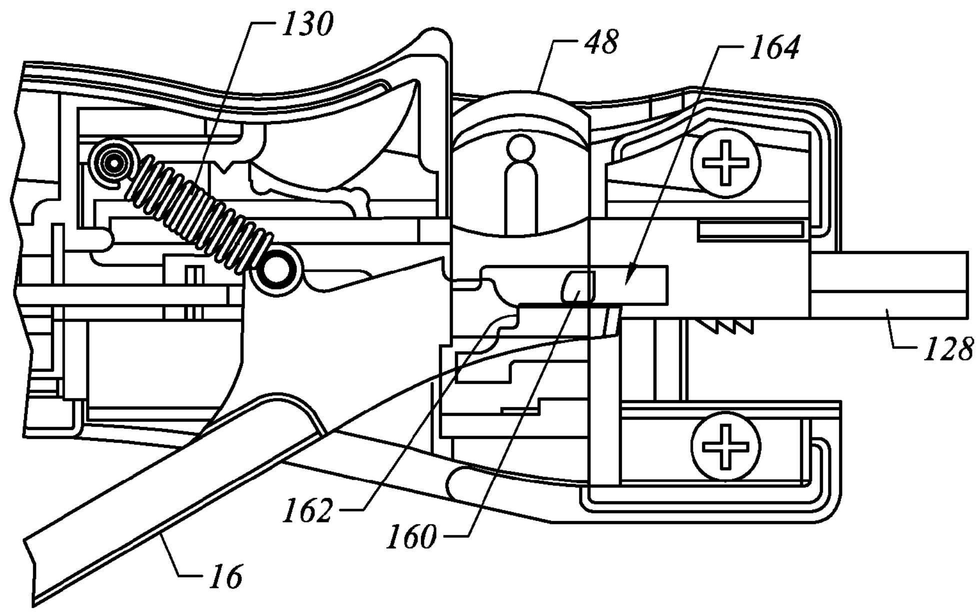
FIGS. 23A and 23B illustrate a side view of a partially exposed handle showing the retracted secondary driver block and the handle lever disengaged from the secondary driver block.
Figure 23B:
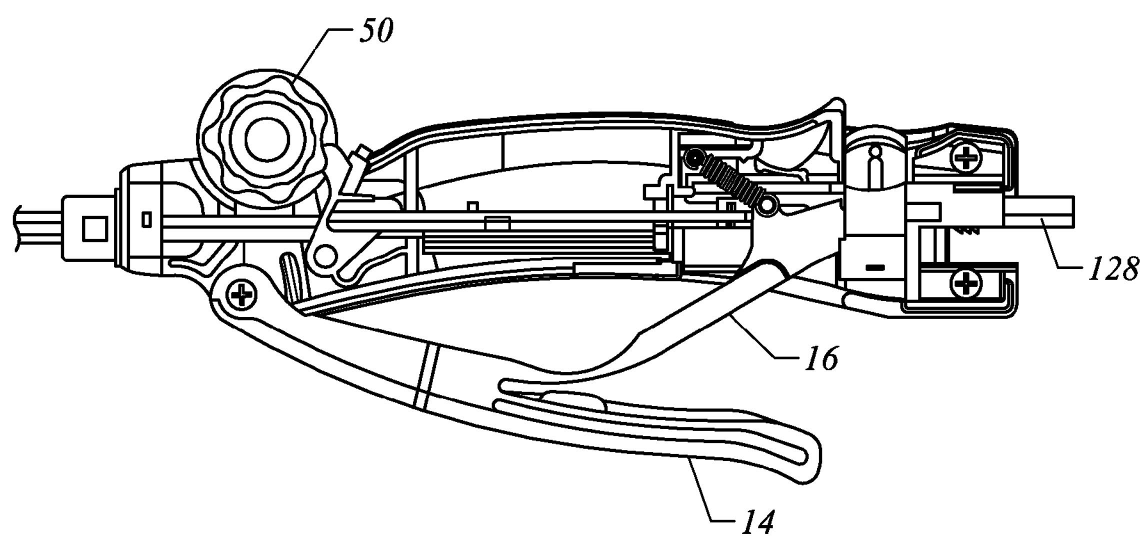

With the suture or wire 54 then tensioned between the implanted anchors 32, 34, secondary anchor 34 may be disengaged from driver 106 and lever 16 may be disengaged from secondary driver block 128 and the inserter assembly 10 removed from the tissue. FIGS. 23A and 23B illustrate a side view of the partially exposed handle 12 showing the retracted secondary driver block 128 and lever 16 disengaged from the secondary driver block 128.

Other modifications and variations can be made to the disclosed embodiments without departing from the subject invention. For example, other arrangements of the anchors and their methods of deployment, including methods of automatically locking the suture within the second anchor, are possible. Similarly, numerous other methods for anchor deployment will be apparent to the skilled artisan. Moreover, the instruments and methods described herein may be utilized in other regions of the body (e.g., knee, hip, etc.) and for other tissue treatment procedures. Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. A method for repairing tissue, comprising:

positioning an inserter of an inserter assembly preloaded with a first and second anchor in proximity to bone;

implanting with the inserter the first anchor with a first end of suture or wire fixedly coupled to the first anchor through the tissue and into a first region of bone;

observing a first depth indicator disposed on the inserter assembly to indicate a suitable depth of insertion of the first anchor within the first portion of bone;

implanting with the inserter the second anchor through the tissue and into a second region of bone observing a second depth indicator disposed on the inserter assembly to indicate a suitable depth of insertion of the second anchor within the second portion of bone; wherein a portion of the suture or wire is slidingly routed through the second anchor and wherein the first anchor and second anchor are separated by a region of tissue to be repaired;

tensioning the suture or wire between the first and second anchors; and locking the suture or wire with respect to the first and second anchors such that the region of tissue to be repaired is affixed to the bone; and wherein the step of locking the suture or wire with respect to the first and second anchor comprises actuating a suture plug member retained within the second anchor so as to lock the suture or wire relative to the second anchor.

2. The method of claim 1 further comprising pre-drilling an opening into the first and second regions of bone prior to implanting the first anchor or implanting the second anchor.

3. The method of claim 1 wherein the method for repairing tissue is performed arthroscopically.

4. The method of claim 1 wherein the first and second region of bone comprise a humeral head.

5. The method of claim 4 wherein the region of tissue to be repaired comprises an articular supraspinatus tendon.

6. The method of claim 1 further comprising locking the first and second anchors within their respective regions of bone prior to tensioning the suture or wire.

7. The method of claim 1 wherein tensioning a suture or wire comprises sliding the suture or wire through the second anchor until the region of tissue to be repaired is maintained against the bone.

8. The method of claim 1 wherein actuating suture plug member comprises retracting the plug member until a portion of the suture or wire is compressed against the plug member and prevented from moving.

9. The method of claim 1 wherein implanting a second anchor comprises placing the second anchor into the second region of bone separately from the first anchor.

10. A method for affixing an articular supraspinatus tendon to a humeral head, comprising:

positioning an inserter of an inserter assembly preloaded with a first and second anchor in proximity to the humeral head;

implanting with the inserter a first anchor through a first portion of the tendon and into a first region of the humeral head, the first anchor having a suture or wire fixedly connected within the first anchor;

observing a first depth indicator disposed on the inserter assembly to indicate a suitable depth of insertion of the first anchor within the first portion of the humeral head;

implanting with the inserter a second anchor through a second portion of the tendon and into a second region of the humeral head, wherein the first anchor and second anchor is separated by a distance, the second anchor having a portion of the suture or wire slidingly routed through the second anchor and also routed adjacent an anchor plug retained within the second anchor;

observing a second depth indicator disposed on the inserter assembly to indicate a suitable depth of insertion of the second anchor within the second portion of the humeral head;

tensioning the suture or wire between the first and second anchors and sliding the anchor plug to lock the suture or wire within the second anchor such that the tendon is affixed to the humeral head.

11. A method of repairing a piece of soft tissue, comprising:

inserting a first anchor through a first portion of soft tissue and into a first portion of bone, said first anchor detachably connected with a distal end of a first support sleeve within a first inserter shaft of an inserter assembly;

observing a first depth indicator disposed on the inserter assembly to indicate a suitable depth of insertion of the first anchor within the first portion of bone;

locking said first anchor with the first portion of bone ;

detaching said first anchor from said first support sleeve;

inserting a second anchor through a second portion of soft tissue spaced away from the first portion of soft tissue and into a second portion of bone, said second anchor detachably connected with a distal end of a second support sleeve within a second inserter shaft of the inserter assembly;

observing a second depth indicator disposed on the inserter assembly to indicate a suitable depth of insertion of the second anchor within the second portion of bone;

locking said second anchor with second portion of bone;

adjusting the tension of a connecting member that is fixedly connected with the first anchor and slidingly routed through the second anchor, said connecting member also connected with the inserter assembly, so as to repair the piece of soft tissue; and detaching the second anchor from the second support sleeve; wherein before the step of detaching the second anchor, actuating a suture plug retained within the second anchor so as to lock the connecting member relative to the second anchor.

12. The method of claim 11 wherein the step of actuating a suture plug comprises, retracting the suture plug to lock the connecting member relative to the second anchor.

* * * * *